(12) United States Patent
Felder et al.

(10) Patent No.: US 10,667,856 B2
(45) Date of Patent: Jun. 2, 2020

(54) ROBOTIC BI-POLAR INSTRUMENTS

(71) Applicant: Ethicon LLC, Guaynabo, PR (US)

(72) Inventors: Kevin D. Felder, Cincinnati, OH (US); Michel G. Bruehwiler, Newton, MA (US); Cole Constantineau, Cambridge, MA (US); Daniel J. Yasevac, Arlington, MA (US); Mary T. Carter, Boston, MA (US); Jeffrey Chagnon, Somerville, MA (US); Kevin DelSignore, Brighton, MA (US)

(73) Assignee: Ethicon LLC, Guaynabo, PR (US)

( * ) Notice: Subject to any disclaimer, the term of this patent is extended or adjusted under 35 U.S.C. 154(b) by 447 days.

(21) Appl. No.: 15/451,483

(22) Filed: Mar. 7, 2017

(65) Prior Publication Data

US 2017/0252096 A1    Sep. 7, 2017

Related U.S. Application Data

(60) Provisional application No. 62/304,716, filed on Mar. 7, 2016.

(51) Int. Cl.
*A61B 18/14* (2006.01)
*A61B 34/00* (2016.01)
(Continued)

(52) U.S. Cl.
CPC .......... *A61B 18/1445* (2013.01); *A61B 17/32* (2013.01); *A61B 34/30* (2016.02);
(Continued)

(58) Field of Classification Search
CPC ............ A61B 18/1442; A61B 18/1445; A61B 18/1447; A61B 17/29; A61B 2017/2926;
(Continued)

(56) References Cited

U.S. PATENT DOCUMENTS 8,114,345 B2   2/2012  Dlugos, Jr. et al.
8,333,780 B1 * 12/2012  Pedros .................. A61B 17/29
                                                                    600/37

(Continued)

FOREIGN PATENT DOCUMENTS

WO   WO-2014151621 A1   9/2014
WO   WO-2014151952 A1   9/2014

OTHER PUBLICATIONS

U.S. Appl. No. 15/200,283 entitled "Methods, Systems, and Devices for Initializing a Surgical Tool", filed Jul. 1, 2016.

(Continued)

*Primary Examiner* — Linda C Dvorak
*Assistant Examiner* — Khadijeh A Vahdat
(74) *Attorney, Agent, or Firm* — Mintz Levin Cohn Ferris Glovsky and Popeo, P.C.

(57) ABSTRACT

Various exemplary systems, devices, and methods for robotic bi-polar instruments are provided. In general, a surgical tool can include an elongate shaft, an end effector, a wrist that couples the end effector to the shaft at a distal end of the shaft, and a tool housing coupled to a proximal end of the shaft that is configured to control the operation various features associated with the end effector and to operatively couple to a robotic surgical system.

20 Claims, 38 Drawing Sheets

(51) Int. Cl.
*A61B 34/30* (2016.01)
*A61B 17/32* (2006.01)
*A61B 17/29* (2006.01)
*A61B 18/12* (2006.01)
*A61B 17/00* (2006.01)
*A61B 17/062* (2006.01)
*A61B 46/10* (2016.01)
*A61B 50/30* (2016.01)
*A61B 18/00* (2006.01)

(52) U.S. Cl.
CPC ............ *A61B 34/71* (2016.02); *A61B 17/062* (2013.01); *A61B 46/10* (2016.02); *A61B 50/30* (2016.02); *A61B 2017/00309* (2013.01); *A61B 2017/00327* (2013.01); *A61B 2017/00477* (2013.01); *A61B 2017/2927* (2013.01); *A61B 2017/2932* (2013.01); *A61B 2017/2943* (2013.01); *A61B 2018/00184* (2013.01); *A61B 2018/126* (2013.01); *A61B 2018/1452* (2013.01); *A61B 2018/1455* (2013.01); *A61B 2034/302* (2016.02); *A61B 2034/305* (2016.02); *A61B 2034/306* (2016.02)

(58) Field of Classification Search
CPC .... A61B 2017/2932; A61B 2017/2939; A61B 17/062; A61B 17/32; A61B 2017/00309; A61B 2017/00327; A61B 2017/00477; A61B 2017/2927; A61B 2017/2943; A61B 2018/00184; A61B 2018/126; A61B 2018/1452; A61B 2018/1455; A61B 34/30; A61B 34/71; A61B 2034/302; A61B 2034/305; A61B 2034/306
See application file for complete search history.

(56) References Cited

U.S. PATENT DOCUMENTS

| | | | |
|---|---|---|---|
| 8,771,260 B2 * | 7/2014 | Conlon | ............... A61B 17/29 606/1 |
| 9,055,961 B2 | 6/2015 | Manzo et al. | |
| 9,402,682 B2 | 8/2016 | Worrell et al. | |
| 2005/0090817 A1 * | 4/2005 | Phan | ............... A61B 18/1445 606/41 |
| 2009/0112230 A1 | 4/2009 | Jinno | |
| 2011/0251613 A1 * | 10/2011 | Guerra | ............... A61B 17/295 606/52 |
| 2011/0257680 A1 * | 10/2011 | Reschke | ............ A61B 17/285 606/206 |
| 2014/0005718 A1 * | 1/2014 | Shelton, IV | ..... A61B 17/07207 606/205 |
| 2015/0342585 A1 | 12/2015 | Steege | |
| 2016/0270839 A1 | 9/2016 | Stewart et al. | |

OTHER PUBLICATIONS

U.S. Appl. No. 15/237,648 entitled "Methods, Systems, and Devices for Causing End Effector Motion With a Robotic Surgical System", filed Aug. 16, 2016.

U.S. Appl. No. 15/237,653 entitled "Methods, Systems, and Devices for Controlling a Motor of a Robotic Surgical Systems", filed Aug. 16, 2016.

U.S. Appl. No. 15/411,411 entitled "Articulating Electrosurgical Tools", filed Jan. 20, 2017.

International Search Report and Written Opinion for PCT/US2017/021066 dated Jul. 24, 2017 (13 pages).

* cited by examiner

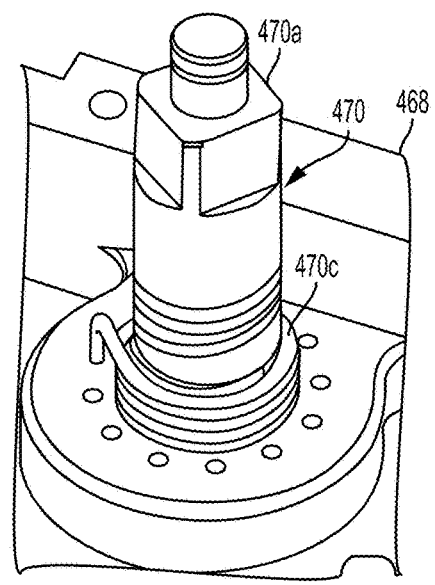
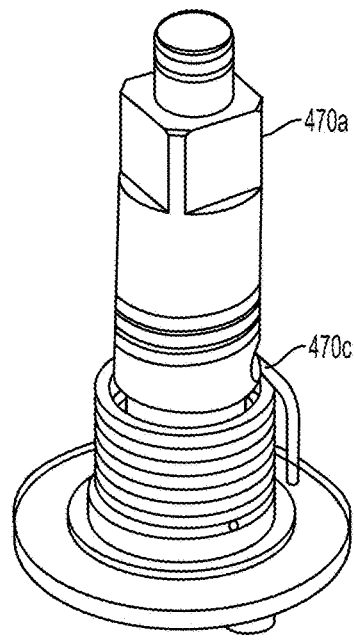
FIG. 26    FIG. 27
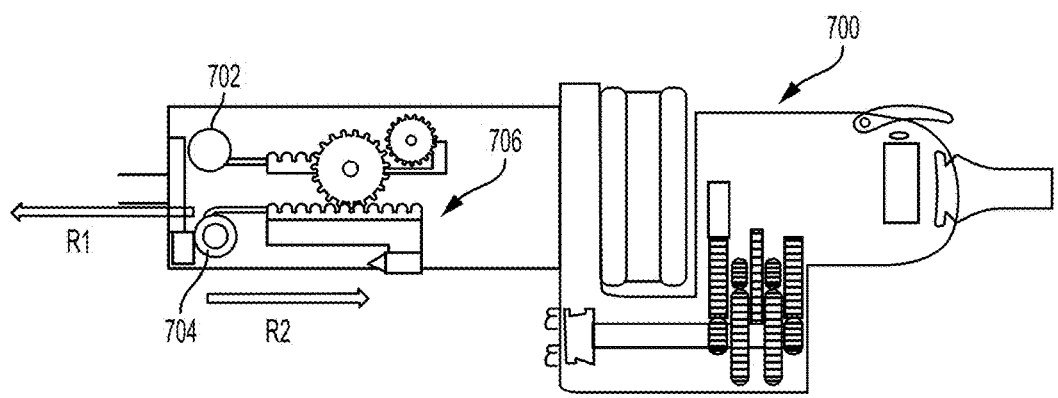
FIG. 28

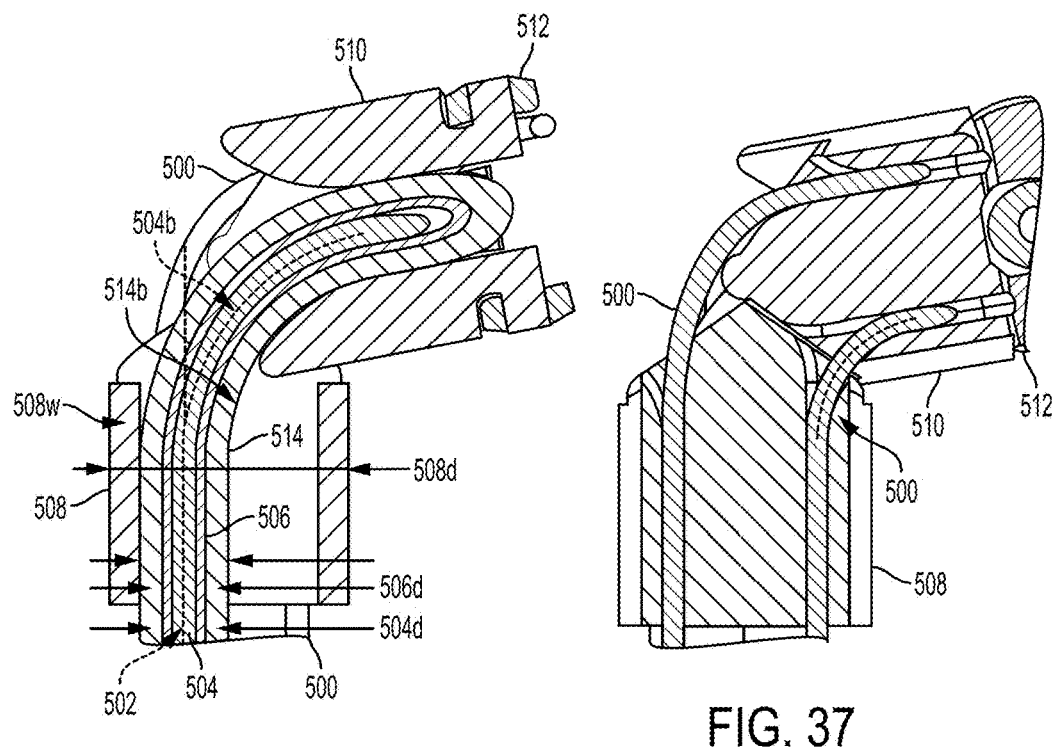
FIG. 36
FIG. 37
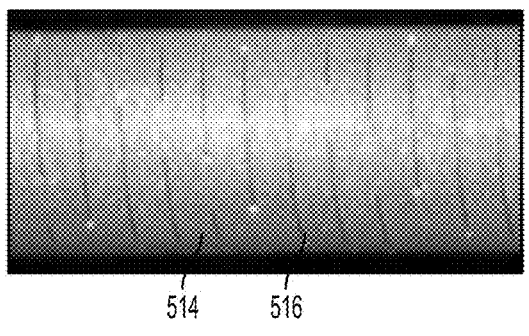
FIG. 38
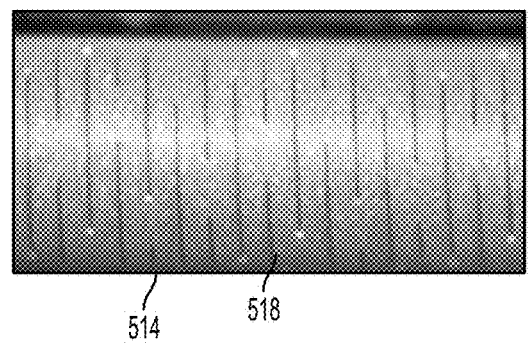
FIG. 39

ROBOTIC BI-POLAR INSTRUMENTS

CROSS REFERENCE

The present application claims priority to U.S. Provisional Patent Application No. 62/304,716 entitled "Robotic Bi-Polar Instruments" filed Mar. 7, 2016, which is hereby incorporated by reference in its entirety.

FIELD

Methods, systems, and devices are provided for robotic surgery, and in particular bi-polar instruments.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity, and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display at a location remote from the patient. The surgeon can typically perform the surgical procedure at the location remote from the patient whilst viewing the end effector movement on the visual display during the surgical procedure. While viewing typically a three-dimensional image of the surgical site on the visual display, the surgeon performs the surgical procedures on the patient by manipulating master control devices at the remote location, which master control devices control motion of the remotely controlled instruments.

While significant advances have been made in the field of robotic surgery, there remains a need for improved methods, systems, and devices for use in robotic surgery.

SUMMARY

In general, systems, devices, and methods for robotic bi-polar instruments are provided.

In one aspect, a surgical device is provided that in one embodiment includes an elongate shaft, a pair of jaws at a distal end of the elongate shaft, a cable configured to be actuated and thereby move in a proximal direction, a slidable member operatively engaged with the cable and being configured to slide in a distal direction in response to the movement of the cable in the proximal direction, and a link operatively coupled with the slidable member and with the cable. The sliding of the slidable member is configured to cause the link to pivot and thereby cause the pair of jaws to open. The pair of jaws are configured to engage tissue therebetween and apply energy thereto.

The surgical device can vary in any number of ways. For example, the surgical device can include a second cable operatively engaged with the slidable member, configured to move in the proximal direction to cause the pair of jaws to close, and configured to slide in the proximal direction in response to the movement of the second cable in the proximal direction, and the sliding of the slidable member in the proximal direction can be configured to cause the link to pivot and thereby cause the pair of jaws to close. In at least some embodiments, the cable can be attached to one of a proximal end and a distal end of the slidable member, and the second cable can be attached to the other of the proximal end and the distal end of the slidable member. In at least some embodiments, the cable can be configured to move in the distal direction when the second cable is moving in the proximal direction, and the second cable can be configured to move in the distal direction when the cable is moving in the proximal direction. In at least some embodiments, the surgical device can include a housing having the elongate shaft extending distally therefrom, and the housing can include a first rotary member configured to rotate to cause the movement of the cable in the distal direction and can include a second rotary member configured to rotate to cause the movement of the second cable in the proximal direction. The housing can be configured to be coupled to a tool driver of a robotic surgical system that provides inputs to the first and second rotary members to cause the rotation thereof.

For another example, the surgical device can include a pulley having the cable operatively engaged therewith, with trailing ends of the cable extending proximally from the pulley. For yet another example, the cable can be configured to be actuated and thereby move in the proximal direction, the slidable member can be configured to slide in the distal direction in response to the movement of the cable in the proximal direction, and the sliding of the slidable member in the distal direction can be configured to cause the link to pivot and thereby cause the pair of jaws to close. For still another example, the surgical device can include a housing having the elongate shaft extending distally therefrom, and the housing can include a first rotary member configured to rotate to cause the movement of the cable in the proximal direction. For another example, the surgical device can include a rod extending along the elongate shaft, and the slidable member can be configured to slide along the rod.

For yet another example, the surgical device can include a bias member that biases the pair of jaws closed. For another example, the surgical device can include an articulation cable configured to be actuated and thereby cause the pair of jaws to articulate relative to the elongate shaft, and an energy cable configured to deliver energy for the pair of jaws to apply to the engaged tissue.

In another embodiment, a surgical device includes an elongate shaft, an end effector configured to engage tissue and apply energy thereto, a cutting element configured to move longitudinally along the end effector to cut tissue engaged by the end effector, a cutting element cable configured to be actuated to cause the movement of the cutting element, and a pulley at a distal end of the end effector and operatively coupled to the cutting element cable such that the cutting element cable slides along the pulley during the movement of the cutting element.

The surgical device can have any number of variations. For example, the cutting element cable can be configured to be pushed distally to cause the movement of the cutting element. For another example, the surgical device can include an articulation cable configured to be actuated and thereby cause the pair of jaws to articulate relative to the elongate shaft, a closure cable configured to be actuated and thereby cause the pair of jaws to close, and an energy cable to configured to deliver energy for the pair of jaws to apply to the engaged tissue.

In another aspect, a surgical method is provided that in one embodiment includes advancing jaws at a distal end of a surgical tool into a patient. The surgical tool is configured to apply energy to tissue engaged by the end effector. The surgical method also includes causing a cable that extends along the elongate shaft to move proximally to thereby cause a slidable member operatively engaged with the cable to slide distally. The distal sliding of the slidable member causes a link to pivot and thereby cause the jaws to open.

The surgical method can vary in any number of ways. For example, the surgical method can include causing a second cable that extends along the elongate shaft to move proximally to thereby cause the slidable member operatively engaged with the second cable to slide proximally. The proximal sliding of the slidable member in response to the movement of the second cable can cause the link to pivot and thereby cause the jaws to close. In at least some embodiments, causing the cable to move proximally includes providing an input to the surgical tool from a robotic surgical system having the surgical tool coupled thereto, and causing the second cable to move proximally includes providing another input to the surgical tool from the robotic surgical system having the surgical tool coupled thereto.

For another example, the surgical method can include causing the cable to move distally to thereby cause the slidable member to slide proximally. The proximal sliding of the slidable member can cause the link to pivot and thereby cause the jaws to close.

For yet another example, causing the cable to move proximally can include providing an input to the surgical tool from a robotic surgical system having the surgical tool coupled thereto.

BRIEF DESCRIPTION OF THE DRAWINGS

The invention will be more fully understood from the following detailed description taken in conjunction with the accompanying drawings, in which:

FIG. 26 is a perspective view of a portion of the tool housing of FIG. 23 including a winch and bias member;

FIG. 27 is a perspective view of the winch and bias member of FIG. 26;

FIG. 28 is a side, partially transparent schematic view of a proximal portion of yet another embodiment of a surgical tool;

FIG. 36 is a side cross-sectional view of a portion of the tool of FIG. 35;

FIG. 37 is a side view of a portion of the tool of FIG. 35;

FIG. 38 is a side view of a portion of one embodiment of a hypotube;

FIG. 39 is a side view of a portion of another embodiment of a hypotube;

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary systems, devices, and methods for robotic bi-polar instruments are provided.

Figure 1:
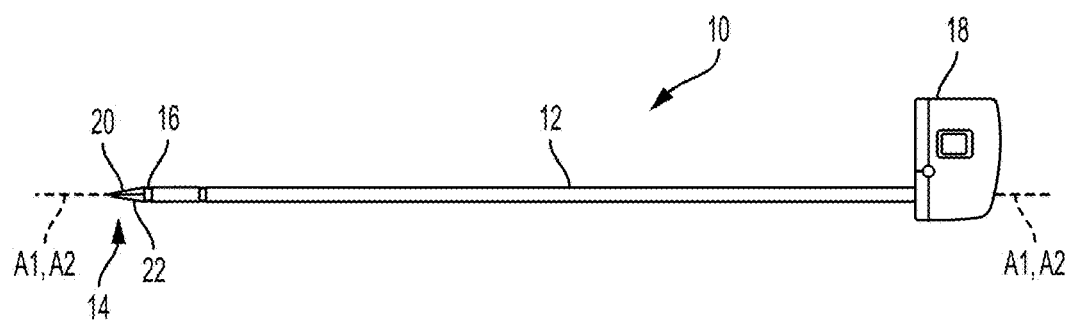
FIG. 1 is a side schematic view of one embodiment of a surgical tool.

FIG. 1 illustrates one embodiment of a surgical tool 10 that includes an elongate shaft 12, an end effector 14, a wrist 16 that couples the end effector 14 to the shaft 12 at a distal end of the shaft 12, and a tool housing 18 coupled to a proximal end of the shaft 12. The end effector 14 is configured to move relative to the shaft 12 at the wrist 16, e.g., by pivoting at the wrist 16, to position the end effector 14 at a desired location relative to a surgical site during use of the tool 10. The housing 18 includes various components (e.g., gears and/or actuators) configured to control the operation various features associated with the end effector 14 (e.g., any one or more of clamping, firing, rotation, articulation, energy delivery, etc.). In at least some embodiments, the shaft 12, and hence the end effector 14 coupled thereto, is configured to rotate about a longitudinal axis A1 of the shaft 12. In such embodiments, the various components of the housing 18 are configured to control the rotational movement of the shaft 12. In at least some embodiments, as in this illustrated embodiment, the surgical tool 10 is configured to releasably couple to a robotic surgical system, and the tool housing 18 can include coupling features configured to allow the releasable coupling of the tool 10 to the robotic surgical system. Each of the shaft 12, end effector 14, wrist 16, and housing 18 are discussed further below.

The surgical tool 10 can have any of a variety of configurations. In general, the surgical tool can be configured to perform at least one surgical function and can include any of, for example, forceps, a grasper, a needle driver, scissors, an electrocautery tool that applies energy, a stapler, a clip applier, a suction tool, an irrigation tool, an imaging device (e.g., an endoscope or ultrasonic probe), etc. The surgical tool 10 in at least some embodiments is configured to apply energy (such as radiofrequency (RF) energy) to tissue, while in other embodiments the tool 10 is not configured to apply energy to tissue.

The shaft 12 can have any of a variety of configurations. In general, the shaft 12 is an elongate member extending distally from the housing 18 and having at least one inner lumen extending therethrough. The shaft 12 is fixed to the housing 18, but in other embodiments the shaft 12 can be releasably coupled to the housing 18 such that the shaft 12 can be interchangeable with other shafts. This may allow a single housing 18 to be adaptable to various shafts having different end effectors.

The end effector 14 can have a variety of sizes, shapes, and configurations. The end effector 14 includes a tissue grasper having a pair of opposed jaws 20, 22 configured to move between open and closed positions with one or both of the jaws 20, 22 configured to pivot at the wrist 16 to move the end effector 14 between the open and closed positions. The end effector 14 in other embodiments can have other configurations, e.g., scissors, a babcock, a retractor, etc.

The wrist 16 can have any of a variety of configurations. Exemplary embodiments of a wrist of a surgical tool and of effecting articulation at the wrist are described in International Pat. Pub. No. WO 2014/151952 entitled "Compact Robotic Wrist" filed on Mar. 13, 2014, International Pat. Pub. No. WO 2014/151621 entitled "Hyperdexterous Surgical System" filed on Mar. 13, 2014, U.S. Pat. No. 9,055,961 entitled "Fusing And Cutting Surgical Instrument And Related Methods" filed on Feb. 17, 2012, U.S. patent application Ser. No. 15/200,283 entitled "Methods, Systems, And Devices For Initializing A Surgical Tool" filed on Jul. 1, 2016, and U.S. patent application Ser. No. 15/237,648 entitled "Methods, Systems, And Devices For Causing End Effector Motion With A Robotic Surgical System" filed on Aug. 16, 2016, which are hereby incorporated by reference in their entireties. In general, the wrist 16 can include a joint configured to allow movement of the end effector 14 relative to the shaft 12, such as a pivot joint at which the jaws 20, 22 are pivotally attached. In some embodiments, the pivoting motion can include pitch movement about a first axis of the wrist 16 (e.g., a X axis), yaw movement about a second axis of the wrist 16 (e.g., a Y axis), and combinations thereof to allow for 360° rotational movement of the end effector 14 about the wrist 16. In other embodiments, the pivoting motion can be limited to movement in a single plane, e.g., only pitch movement about the first axis of the wrist 16 or only yaw movement about the second axis of the wrist 16, such that end effector 14 rotates in a single plane.

Figure 2:
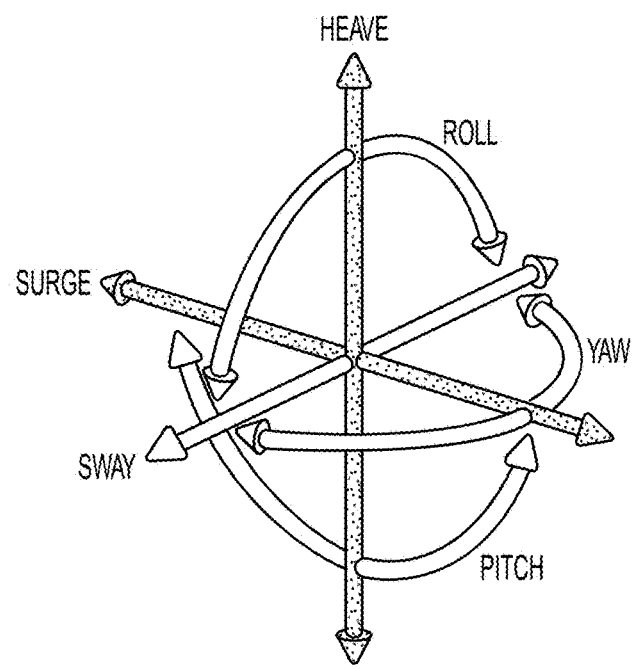
FIG. 2 is a graphical representation of terminology associated with six degrees of freedom.

FIG. 2 illustrates degrees of freedom of a system represented by three translational or position variables, e.g., surge, heave, sway, and by three rotational or orientation variables, e.g., Euler angles or roll, pitch, yaw, that describe the position and orientation of a component of a surgical system with respect to a given reference Cartesian frame. As used herein, and as illustrated in FIG. 2, the term "surge" refers to forward and backward movement, the term "heave" refers to movement up and down, and the term "sway" refers to movement left and right. With regard to the rotational terms, "roll" refers to tilting side to side, "pitch" refers to tilting forward and backward, and "yaw" refers to turning left and right.

The movement of the end effector 14 in this illustrated embodiment includes articulating movement of the end effector 14 between an unarticulated position, in which the end effector 14 is substantially longitudinally aligned with the shaft 12 (e.g., a longitudinal axis A2 of the end effector 14 is substantially aligned with the longitudinal axis A1 of the shaft 12 such that the end effector 14 is at a substantially zero angle relative to the shaft 12), and an articulated position, in which the end effector 14 is angularly orientated relative to the shaft 12 (e.g., the longitudinal axis A2 of the end effector 14 is angled relative to the longitudinal axis A1 of the shaft 12 such that the end effector 14 is at a non-zero angle relative to the shaft 12). A person skilled in the art will appreciate that the end effector 14 may not be precisely aligned with the shaft 12 (e.g., may not be at a precise zero angle relative thereto) but nevertheless be considered to be aligned with the shaft 12 (e.g., be at a substantially zero angle) due to any number of factors, such as manufacturing tolerance and precision of measurement devices. The end effector 14 is shown in the unarticulated position in FIG. 1. The movement of the end effector 14 in this illustrated embodiment also includes rotational movement of the end effector 14 in which the end effector 14 rotates about its longitudinal axis A2, either with or without corresponding rotation of the shaft 12 about its longitudinal axis A1.

The surgical tool 10 can include one or more actuation shafts configured to facilitate movement of the end effector 14. Each of the one or more actuation shafts can extend along the shaft 12 (e.g., in an inner lumen thereof) and can be operatively coupled to the housing 18 and to the end effector 14. In this way, a tool driver coupled to the housing 18 can be configured to provide input to the surgical tool 10 via the tool housing 18 and thereby actuate the one or more actuation shafts to cause movement of the end effector 14.

The systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the robotic surgical system can be wired, all electronic communication in the robotic surgical system can be wireless, or some portions of the robotic surgical system can be in wired communication and other portions of the system can be in wireless communication.

Figure 3:
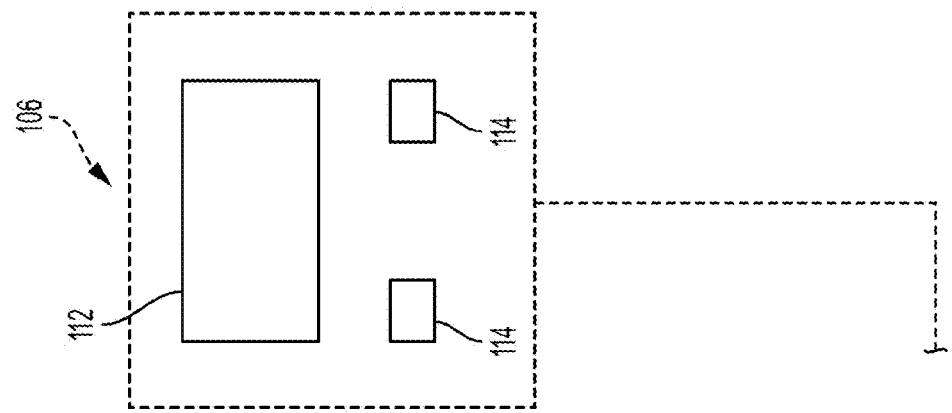
FIG. 3 is a perspective view of one embodiment of a robotic surgical system that includes a patient-side portion and a user-side portion.
Figure 3:
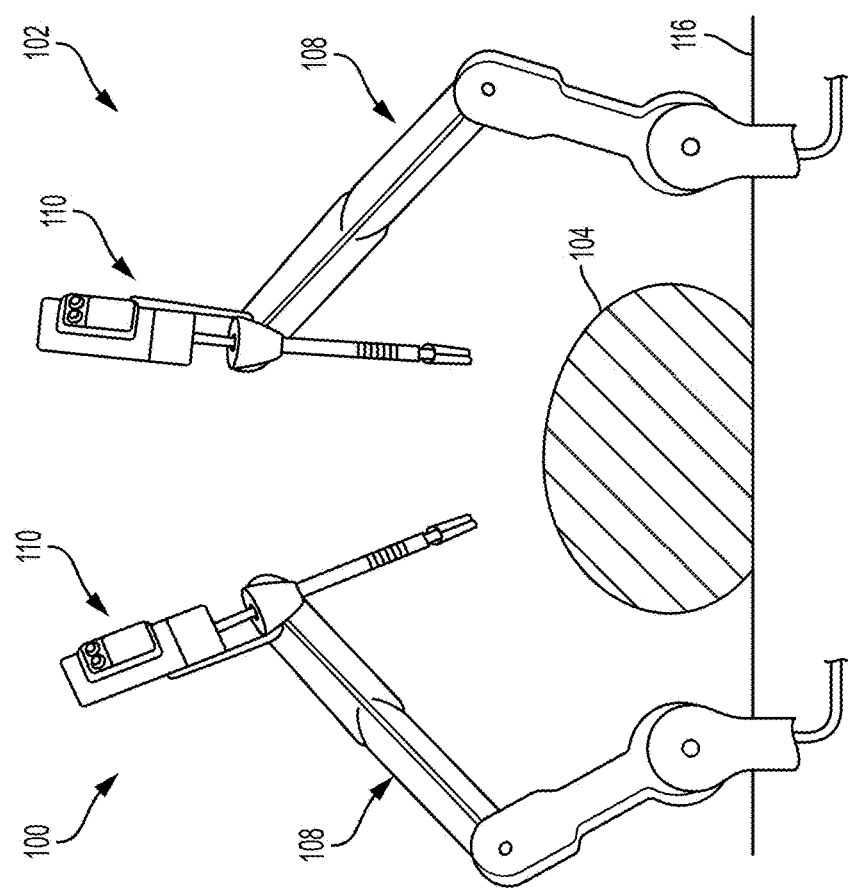

FIG. 3 is a perspective view of one embodiment of a robotic surgical system 100 that includes a patient-side portion 102 that is positioned adjacent to a patient 104, and a user-side portion 106 that is located a distance from the patient, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 112 for viewing the patient 104 and/or surgical site, and a control system 114 for controlling the movement of the robotic arms 108 and each tool assembly 110 during a surgical procedure.

The control system 114 can have a variety of configurations and can be located adjacent to the patient in the operating room), remote from the patient (e.g., in a separate control room), or distributed at two or more locations (e.g., the operating room and/or separate control room(s)). As an example of a distributed system, a dedicated system control console can be located in the operating room, and a separate console can be located in a remote location. The control system 114 can include components that enable a user to view a surgical site of the patient 104 being operated on by the patient-side portion 102 and/or to control one or more part of the patient-side portion 102 (e.g., to perform a surgical procedure at the surgical site). In some embodiments, the control system 114 can also include one or more manually-operated input devices, such as a joystick, exoskeletal glove, a powered and gravity-compensated manipulator, or the like. The one or more input devices can control teleoperated motors which, in turn, control the movement of the surgical system, including the robotic arms 108 and tool assemblies 110.

The patient-side portion 102 can have a variety of configurations. As illustrated in FIG. 3, the patient-side portion 102 can couple to an operating table 116. However, in other embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 3). Alternatively, the patient-side portion 102 can include a single assembly that includes one or more robotic arms 108 extending therefrom.

Figure 4:
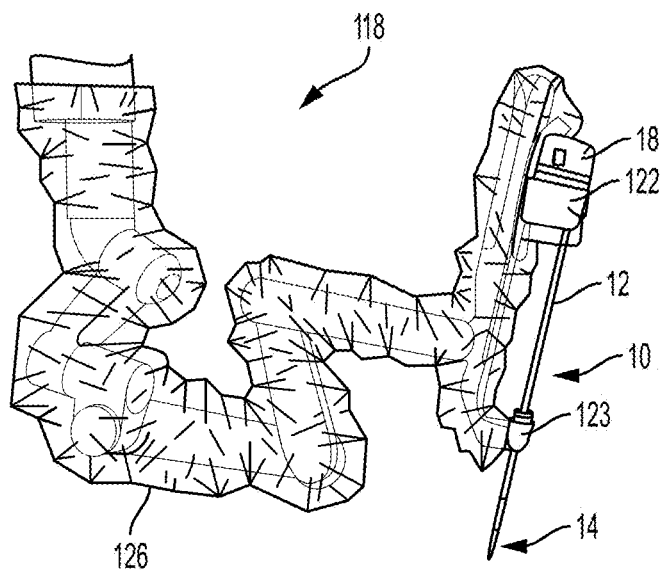
FIG. 4 is a perspective view of one embodiment of a robotic arm of a robotic surgical system with the surgical tool of FIG. 1 releasably and replaceably coupled to the robotic arm.

FIG. 4 illustrates another embodiment of a robotic arm 118 and the surgical tool 10 of FIG. 1 releasably and replaceably coupled to the robotic arm 118. Other surgical instruments can instead be coupled to the arm 118, as discussed herein. The robotic arm 118 is configured to support and move the associated tool 10 along one or more degrees of freedom (e.g., all six Cartesian degrees of freedom, five or fewer Cartesian degrees of freedom, etc.).

The robotic arm 118 can include a tool driver 122 at a distal end of the robotic arm 118, which can assist with controlling features associated with the tool 10. The robotic arm 118 can also include an entry guide 123 (e.g., a cannula mount, cannula, etc.) that can be a part of or releasably and replaceably coupled to the robotic arm 118, as shown in FIG. 4. A shaft of a tool assembly can be inserted through the entry guide 123 for insertion into a patient, as shown in FIG. 4 in which the shaft 12 of the tool 10 of FIG. 1 is shown inserted through the entry guide 123.

In order to provide a sterile operation area while using the surgical system, a barrier 126 can be placed between the actuating portion of the surgical system (e.g., the robotic arm 118) and the surgical instruments coupled thereto (e.g., the tool 10, etc.). A sterile component, such as an instrument sterile adapter (ISA), can also be placed at the connecting interface between the tool 10 and the robotic arm 118. The placement of an ISA between the tool 10 and the robotic arm 108 can ensure a sterile coupling point for the tool 10 and the robotic arm 118. This permits removal of surgical instruments from the robotic arm 118 to exchange with other surgical instruments during the course of a surgery without compromising the sterile surgical field.

Figure 5:
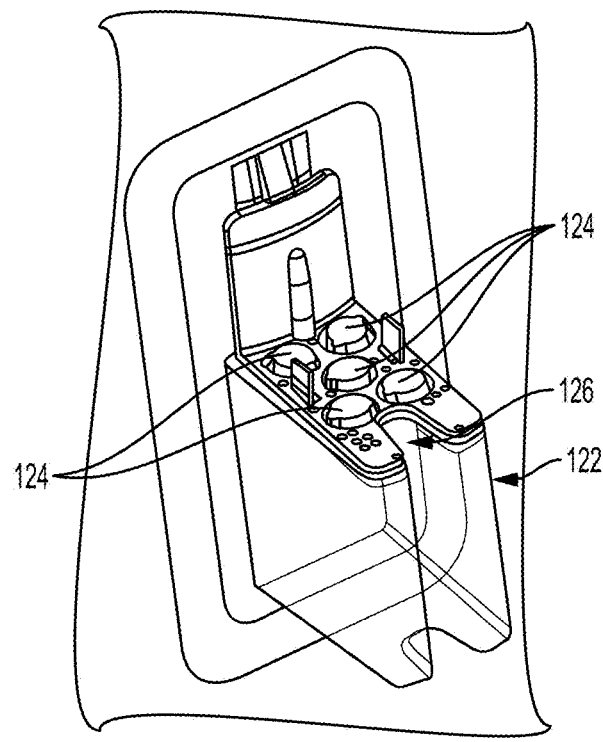
FIG. 5 is a perspective view of a tool driver of the robotic arm of FIG. 4.

FIG. 5 illustrates the tool driver 122 in more detail. As shown, the tool driver 122 includes one or more motors, e.g., five motors 124 are shown, that control a variety of movements and actions associated with the tool 10 coupled to the arm 118. For example, each motor 124 can couple to and/or interact with an activation feature (e.g., gear) associated with the tool 10 for controlling one or more actions and movements that can be performed by the tool 10, such as for assisting with performing a surgical operation. The motors 124 are accessible on the upper surface of the tool driver 122, and thus the tool 10 (e.g., the housing 18 thereof) is configured to mount on top of the tool driver 122 to couple thereto. Exemplary embodiments of motor operation and components of a tool housing (also referred to as a "puck") configured to controlled by tool driver motors are further described in previously mentioned International Patent Publication No. WO 2014/151952 entitled "Compact Robotic Wrist" filed on Mar. 13, 2014 and International Patent Publication No. WO 2014/151621 entitled "Hyperdexterous Surgical System" filed on Mar. 13, 2014, U.S. patent application Ser. No. 15/200,283 entitled "Methods, Systems, And Devices For Initializing A Surgical Tool" filed on Jul. 1, 2016, and in U.S. patent application Ser. No. 15/237,653 entitled "Methods, Systems, And Devices For Controlling A Motor Of A Robotic Surgical Systems" filed on Aug. 16, 2016, which is hereby incorporated by reference in its entirety.

The tool driver 122 also includes a shaft-receiving channel 126 formed in a sidewall thereof for receiving the shaft 12 of the tool 10. In other embodiments, the shaft 12 can extend through on opening in the tool driver 122, or the two components can mate in various other configurations.

Figure 6:
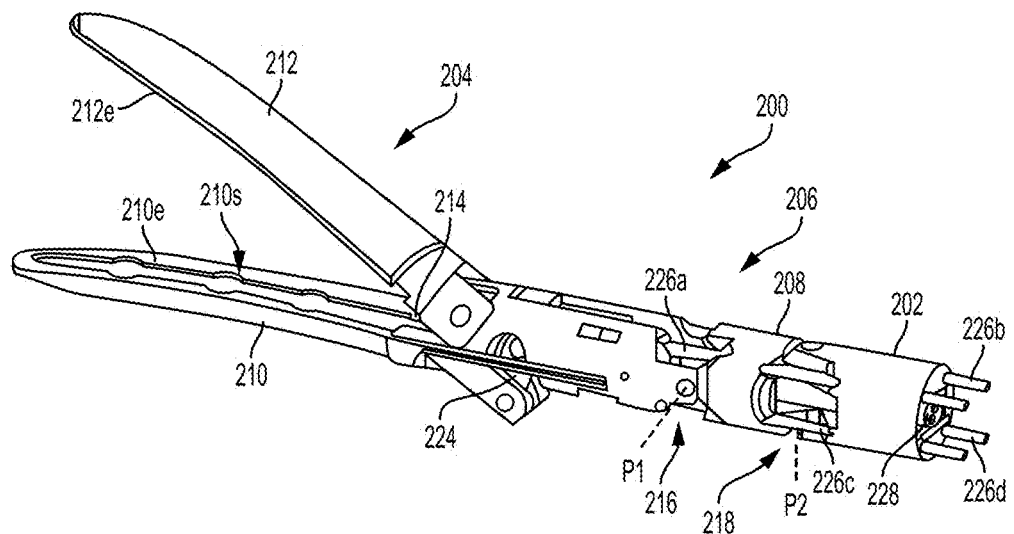
FIG. 6 is a perspective view of a distal portion of another embodiment of a surgical tool.
Figure 7:
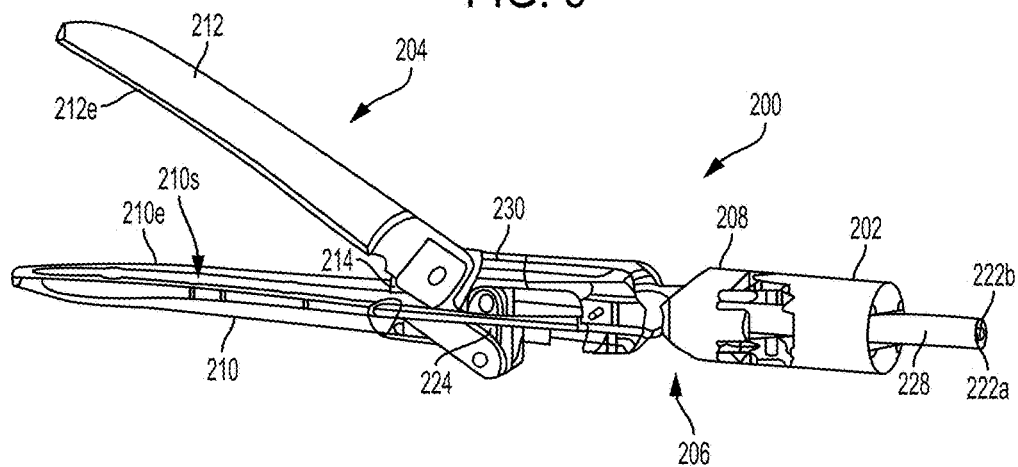
FIG. 7 is another perspective, partially transparent view of a distal portion of the tool of FIG. 6.

FIGS. 6-9 illustrate one embodiment of a surgical tool 200 configured to apply energy to tissue, e.g., is an electrosurgical tool. The tool 200 is generally configured and used similar to the tool 10 of FIG. 1, e.g., includes an elongate shaft 202, an end effector 204, a wrist 206 that couples the end effector 204 to the shaft 202 at a distal end of the shaft 202, and a tool housing (not shown) coupled to a proximal end of the shaft 202. The tool housing can include a plurality of input interfaces configured to operatively couple a tool driver of a surgical robot to the surgical tool 200. The end effector 204 in this illustrated embodiment includes opposed lower and upper jaws 210, 212. As shown in FIGS. 6 and 7, each of the lower and upper jaws 210, 212 includes an electrode 210e, 212e configured to deliver energy to tissue engaged between the jaws 210, 212, such as by each of the electrodes 210e, 212e receiving one pole from a bipolar energy source to create bipolar energy between the electrodes sufficient to fuse tissue. Each of the lower and upper jaws 210, 212 also includes a slot or groove 210s (the upper jaw's slot or groove is obscured in the figures) extending longitudinally therealong that is configured to slidably receive a cutting element 214 therein to allow the cutting element 214 to cut tissue engaged between the jaws 210, 212. Exemplary embodiments of electrosurgical surgical tools configured to apply energy to tissue including are further described in previously mentioned U.S. Pat. No. 9,055,961 entitled "Fusing And Cutting Surgical Instrument And Related Methods" filed on Feb. 17, 2012.

Figure 7A:
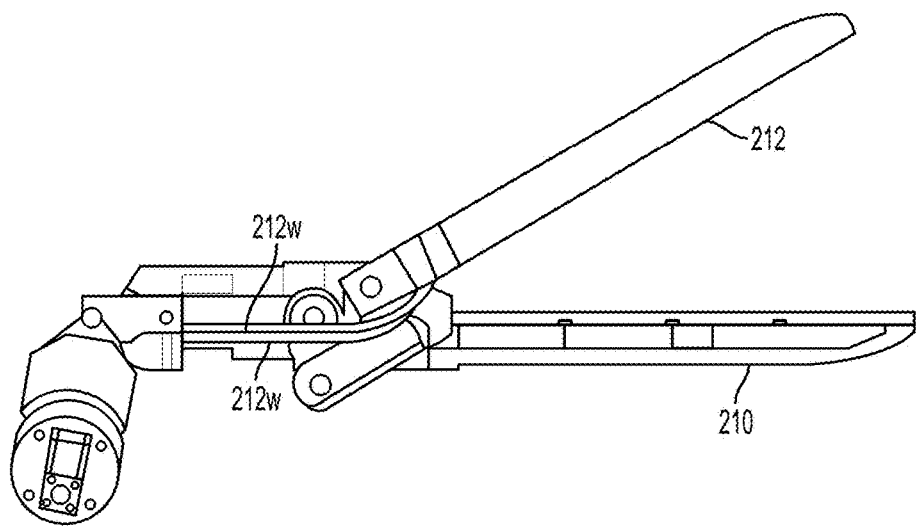
FIG. 7A is yet another perspective, partially transparent view of a distal portion of the tool of FIG. 6.
Figure 8:
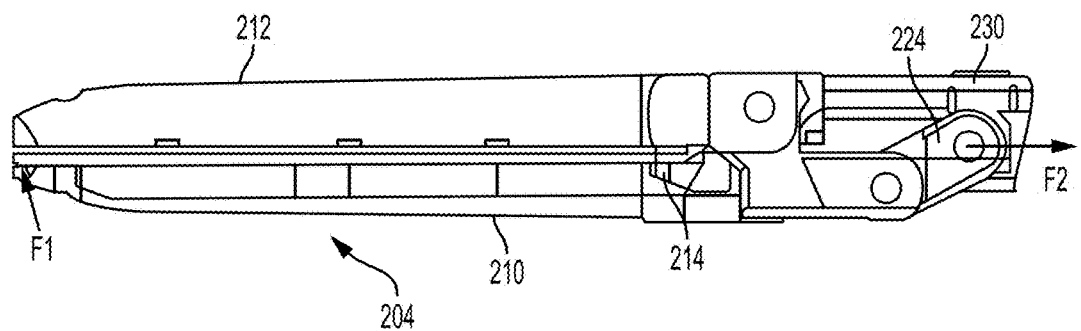
FIG. 8 is a side view of a distal portion of the tool of FIG. 6.
Figure 8A:
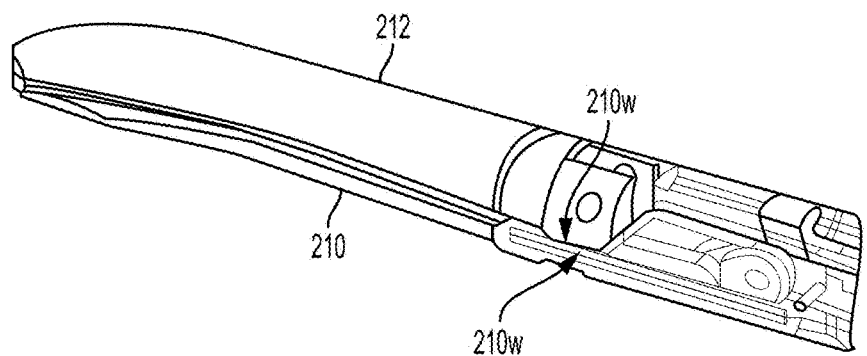
FIG. 8A is another perspective, partially transparent view of a distal portion of the tool of FIG. 6.
Figure 8B:
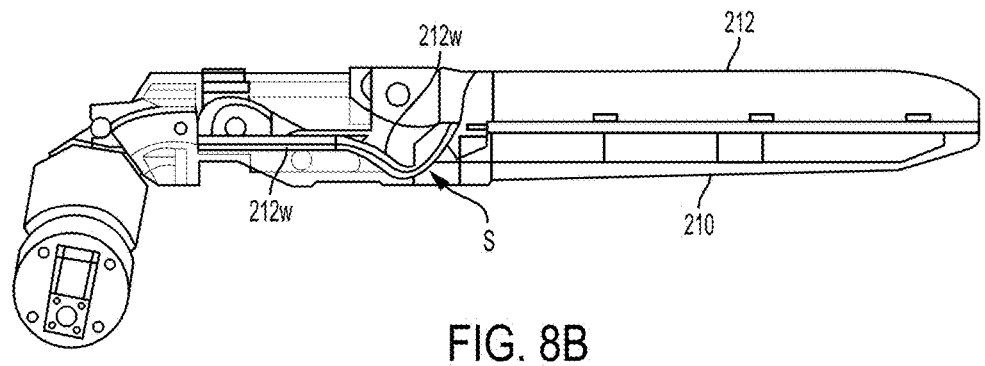
FIG. 8B is still another perspective, partially transparent view of a distal portion of the tool of FIG. 6.

In general, the wrist 206 can allow for fine movements and angulation of the end effector 204 relative to the elongate shaft 202 to which the end effector 204 is coupled. The tool 200 includes one linkage 208 at the wrist 206 that couples the end effector 204 and shaft 202 together. The linkage 208 is configured to facilitate articulation of the end effector 204 relative to the elongate shaft 202, e.g., angle the end effector 204 relative to a longitudinal axis of the elongate shaft 202. A distal end of the linkage 208 is pivotally coupled at a first or distal joint 216 to a proximal end of the end effector 204, e.g., to a proximal end of the bottom jaw 210. A proximal end of the linkage 208 is pivotally coupled at a second or proximal joint 218 to a distal end of the shaft 202. The first joint 216 defines a first pivot axis P1 about which the end effector 204 is configured to pivot relative to the linkage 208. The first joint 216 thus defines a first plane in which the end effector 204 is configured to move relative to the shaft 202. The second joint 218 defines a second pivot axis P2 about which the linkage 208, and hence also the end effector 204 coupled thereto, is configured to pivot relative to the shaft 202. The second joint 218 thus defines a second plane in which the end effector 204 is configured to move relative to the shaft 202. FIGS. 6-8A and 9 show the end effector 204 in an unarticulated position. FIGS. 7A and 8B show the end effector 204 in an articulated position, in this illustrated example with the end effector 204 articulated to the right.

The tool 200 includes first, second, third, and fourth articulation cables 226*a*, 226*b*, 226*c*, 226*d* configured to be actuated to cause articulating movement of the end effector 204 coupled thereto. The articulation cables 226*a*, 226*b*, 226*c*, 226*d* are operatively coupled to the tool housing and are thus configured to be operatively coupled to a tool driver, via the tool housing. Input from the tool driver to the tool housing can thus be configured to actuate the articulation cables 226*a*, 226*b*, 226*c*, 226*d* to cause selective movement of selected one or more of the articulation cables 226*a*, 226*b*, 226*c*, 226*d* to cause selected articulation of the end effector 204.

In this illustrated embodiment, the articulation cables 226*a*, 226*b*, 226*c*, 226*d* are each offset from the first and second pivot axes P1, P2 and hence are each offset from the first and second planes respectively defined by the first and second pivot axes P1, P2. In other words, the articulation cables 226*a*, 226*b*, 226*c*, 226*d* are not on either axis P1, P2 of articulation motion. The articulation cables 226*a*, 226*b*, 226*c*, 226*d* are also spaced radially around the longitudinal axis of the elongate shaft 202 equidistantly from one another at about 45° from the axes P1, P2. This positioning of the articulation cables 226*a*, 226*b*, 226*c*, 226*d* may allow for the end effector 204 to articulate at a maximum articulation angle in each of pitch and yaw directions of about 80°, e.g., +/−80° for each axis P1, P2.

The articulation cables 226*a*, 226*b*, 226*c*, 226*d* each extend longitudinally through the linkage 208. Distal ends of each of the articulation cables 226*a*, 226*b*, 226*c*, 226*d* are fixedly coupled to the end effector 204, e.g., to the bottom jaw 210. The articulation cables' distal ends can be enlarged (e.g., have an enlarged diameter as compared to a remainder of the cable's diameter) to facilitate fixed attachment thereof to the end effector 204 via an attachment mechanism such as welding, adhesive, press fit, crimping, etc. For clarity of illustration, the articulation cables 226*a*, 226*b*, 226*c*, 226*d* are omitted from FIG. 8.

The linkage 208 has four channels configured to guide the articulation cables 226*a*, 226*b*, 226*c*, 226*d* at the first and second joints 216, 218 during articulation. The linkage's channels guide the articulation cables 226*a*, 226*b*, 226*c*, 226*d* around the bend at the first and second joints 216, 218, thereby helping to prevent the articulation cables 226*a*, 226*b*, 226*c*, 226*d* from encountering any sharp corners or radii, reducing friction between the articulation cables 226*a*, 226*b*, 226*c*, 226*d* and the linkage 208, and/or helping to prevent the articulation cables 226*a*, 226*b*, 226*c*, 226*d* from twisting or moving radially inward or outward at either of the first and second joints 216, 218 during articulation. Such friction, sharp corners or radii encounters, and twisting or radial movement may exert more force on the articulation cables 226*a*, 226*b*, 226*c*, 226*d*, which may increase wear on the articulation cables 226*a*, 226*b*, 226*c*, 226*d* and thereby reduce their overall life.

The end effector 204 is configured to move between an open position in which the jaws 210, 212 are open and a closed position in which the jaws 210, 212 are closed. The end effector 204 is shown in the open position in FIGS. 6-7A and 9 and is shown in the closed position in FIGS. 8-8B. As shown in FIG. 7, the tool 200 includes first and second closure cables 222*a*, 222*b* configured to be actuated to cause selective opening and closing of the end effector 204. The closure cables 222*a*, 222*b* are operatively coupled to the tool housing and are thus configured to be operatively coupled to a tool driver, via the tool housing. Input from the tool driver to the tool housing can thus be configured to actuate the closure cables 222*a*, 222*b* to cause selective movement of the closure cables 222*a*, 222*b* to cause selected opening and closing of the end effector 204. For clarity of illustration, the closure cables 222*a*, 222*b* are omitted from FIGS. 6 and 7.

Figure 9:
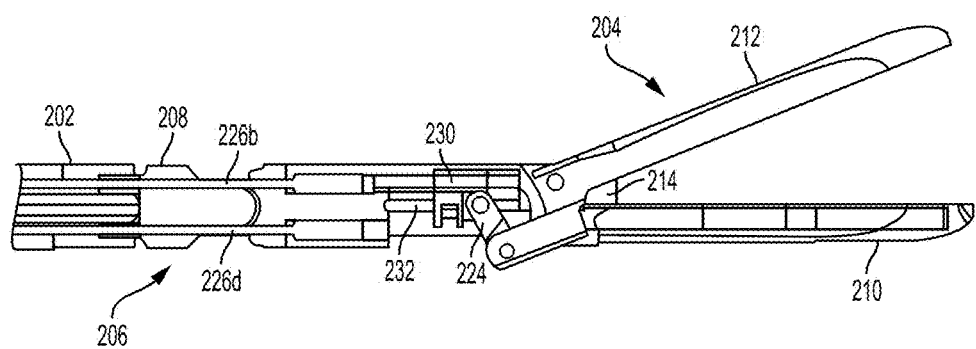
FIG. 9 is a side, partially transparent view of a distal portion of the tool of FIG. 6.

The tool 200 includes a pair of links 224 configured to facilitate the opening and closing of the end effector 204. The links 224 are on opposed sides, e.g., left and right sides, of the end effector 204. The links 224 each have distal ends pivotally attached to a slidable member or hub 230 that is slidably attached to a support rod 232, and each have proximal ends pivotally attached to the upper jaw 212. A distal end of the support rod 240 is attached to the upper jaw 212. In response to the actuation of the first and second closure cables 222*a*, 222*b*, the first and second closure cables 222*a*, 222*b* translate longitudinally, thereby causing the hub 230 to slide either proximally (in response to the closure cables 222*a*, 222*b* being pulled proximally) or distally (in response to the closure cables 222*a*, 222*b* being pushed distally). Distal movement of the hub 230 (e.g., pushing the closure cables 222*a*, 222*b* in a distal direction) pivots the links 224 downwardly, as shown in FIGS. 6, 7, and 9, to cause the end effector 204 to open. Proximal movement of the hub 230 (e.g., pulling the closure cables 222*a*, 222*b* in a proximal direction) pivots the links 224 upwardly to cause the end effector 204 to close, as shown in FIG. 8.

As mentioned above, the tool 200 includes a cutting element 214 configured to translate along the end effector 204. The cutting element 214 is shown in an initial, proximal position in FIGS. 6-9. The tool 200 includes a cutting element or blade cable configured to be actuated to cause translation of the cutting element 214 along the end effector 204. The cutting element cable is operatively coupled to the tool housing and is thus configured to be operatively coupled to a tool driver, via the tool housing. Input from the tool driver to the tool housing can thus be configured to actuate the cutting element cable to cause movement of the cutting element cable 214 to cause the translation of the cutting element 214 and hence cause the cutting of tissue engaged between the jaws 210, 212.

The tool 200 includes an energy or electrical cable configured to provide energy to the electrodes 210*e*, 212*e* at the end effector 204. The energy cable is operatively coupled to the tool housing and is thus configured to be operatively coupled to a tool driver, via the tool housing. Input from the tool driver to the tool housing can thus be configured to actuate the energy cable to selectively cause energy to be delivered to electrodes 210*e*, 212*e*.

The tool 200 includes at least one electrical wire for each of the electrodes 210*e*, 212*e* that can receive energy from the energy cable and deliver the energy to the electrodes 210*e*, 212*e*. As shown in FIGS. 6, 7, and 8A, the tool 200 has two electrical wires 210*w* for the electrode 210*e* at the bottom jaw 210. These bottom wires 210*w* extend longitudinally and are stationary during opening and closing of the jaws 210, 212. As shown in FIGS. 7A and 8B, the tool 200 has two electrical wires 212*w* for the electrode 212*e* at the upper jaw 212. The upper wires 212w move during opening and closing of the jaws 210, 212. FIG. 8B shows that the upper wires 212w have some slack S when the end effector 204 is closed and that the upper wires 212w lose the slack S when the end effector 204 is open, as shown in FIG. 7A. Having more than one electrical wire for each of the electrodes 210e, 212e may be more space efficient than having only one electrical wire for each of the electrodes 210e, 212e since the multiple wires can each have a smaller diameter than the diameter of a single wire used to provide energy to an electrode. If, as discussed further below, wiring is contained in a heat shrink tube, larger wires, i.e., a single wire for each of the electrodes, may be space efficient.

As shown in FIGS. 6 and 7, the closure cables 222a, 222b, the cutting element cable (omitted for clarity of illustration), and the energy cable (omitted for clarity of illustration) can be disposed in and extend through a central tube 228. The tube 228 may help protect the closure cables 222a, 222b, the cutting element cable, and the energy cable. The cutting element cable can be substantially coaxial with the longitudinal axis of the shaft 202, which may allow the cutting element cable to align linearly with the slots in the end effector 204 through which the cutting element 214 translates and thereby help prevent bucking of the cutting element cable and/or provide straight cutting. As shown in FIG. 7, the closure cables 222a, 222b can each extend substantially parallel to the shaft's longitudinal axis, which may help prevent buckling of the closure cables 222a, 222b during longitudinal movement thereof and/or may help the closure cables 222a, 222b be properly aligned with the opposed sides of the end effector 204 with which they are respectively operatively coupled. The energy cable is above the cutting element cable (as the tool 200 is illustrated in FIGS. 6 and 7) in an exemplary embodiment but can be at another location.

The articulation cables 226a, 226b, 226c, 226d, the closure cables 222a, 222b, the cutting element cable, and the energy cable are flexible at least along the wrist 206 to allow for their bending at the first and second joints 216, 218 at the wrist 206. The tube 228 is flexible at least along the wrist 206 to allow for its being at the wrist 206, such as by the tube 228 being formed of a flexible material such as an elastomer and being relatively thin, e.g., about 0.2 mm thick.

FIG. 8 illustrates a clamping force F1 configured to be provided at a distal tip of the end effector 204 when the end effector 204 is in the closed position. The end effector 204 can provide the clamping force F1 to tissue clamped between the jaws 210, 212. For clarity of illustration, tissue is not shown clamped between the jaws 210, 212 in FIG. 8. FIG. 8 also illustrates an actuation force F2 exerted in a proximal direction on the closure cables 222a, 222b to hold the end effector 204 in the closed position. The pair of links 224 allows the actuation force F2 to be less than in other end effectors, such as end effector using a pin of one jaw that slides in a slot of the other jaw to effect jaw movement, while achieving the same clamping force F1. For example, a clamping force F1 for the end effector 204 can be achieved with an actuation force F2.

Figure 8C:
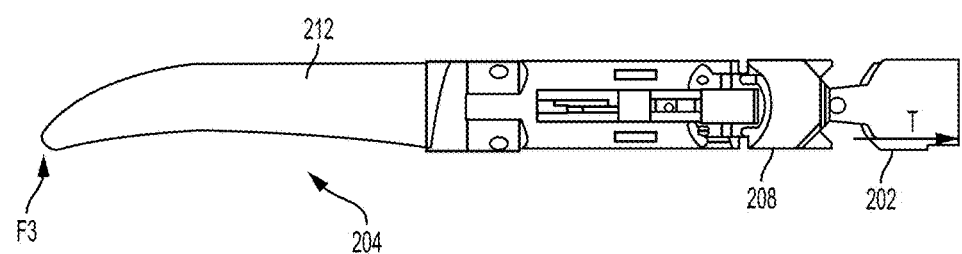
FIG. 8C is a top view of a distal portion of the tool of FIG. 6.

FIG. 8C illustrates a side load or side force F3 at the distal tip of the end effector 204, such as by tissue or other matter pressing against the end effector 204. The articulation cables 226a, 226b, 226c, 226d (and any hypotubes holding the articulation cables 226a, 226b, 226c, 226d) are configured to resist the side force F3 to help prevent the end effector 204 from articulating in response to the side force F3. For example, the articulation cables 226a, 226b, 226c, 226d (and any hypotubes holding the articulation cables 226a, 226b, 226c, 226d) can be configured to resist a side force F3.

Figure 10:
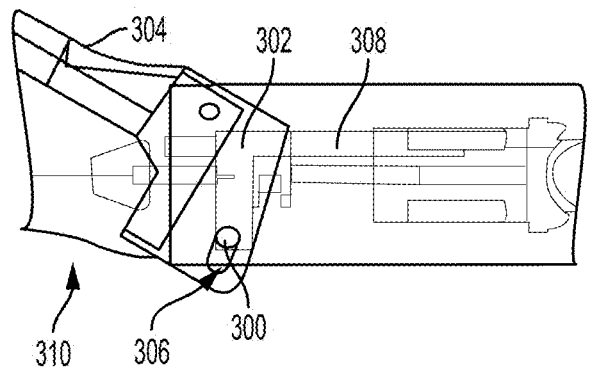
FIG. 10 is a side, partially transparent view of a portion of another embodiment of a surgical tool with an end effector thereof in an open position.
Figure 11:
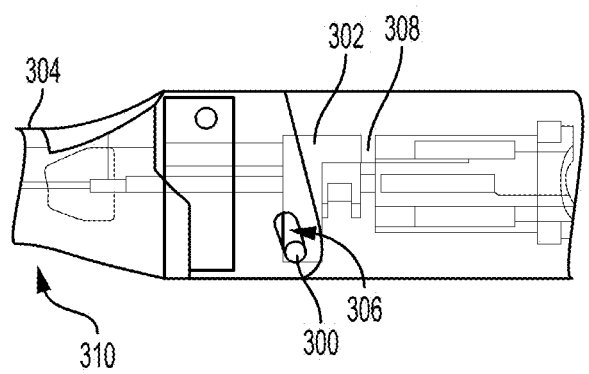
FIG. 11 is a side, partially transparent view of the portion of the tool of FIG. 10 with the end effector in a closed position.

FIGS. 10 and 11 illustrate another embodiment of a surgical tool configured to apply energy to tissue. The tool of FIGS. 10 and 11 is configured and used similar to the tool 200 of FIGS. 6-9 except that it has a different closure mechanism than the tool 200. In the tool 200 of FIG. 6-9, the closure mechanism configured to open and close the end effector 204 includes the links 224, the slidable member 230, and the closure cables 222a, 222b. In the tool of FIGS. 10 and 11, the closure mechanism includes a pair of pins 300 (one of the pins 300 is obscured in FIGS. 10 and 11), a slidable member 302, and first and second closure cables (obscured in FIGS. 10 and 11). The closure mechanism in the illustrated embodiment of FIGS. 10 and 11 does not include links, which may facilitate assembly of the tool. Instead, the tool's upper jaw 304 has a pair of slots 306 formed therein (one of the slots 306 is obscured in FIGS. 10 and 11) that has the pins 300 slidably received therein. The pins 300 extend laterally outward from the slidable member 302, which is slidably attached to a support rod 308. In response to the actuation of the first and second closure cables, the first and second closure cables translate longitudinally, thereby causing the hub 302 to slide either proximally (in response to the closure cables being pulled proximally) or distally (in response to the closure cables being pushed distally). Distal movement of the hub 302 (e.g., pushing the closure cables in a distal direction) causes the pins 300 to slide upwardly in the slots 306, as shown in FIG. 10, to cause the tool's end effector 310 to open. Proximal movement of the hub 302 (e.g., pulling the closure cables in a proximal direction) causes the pins 300 to slide downwardly in the slots 306 to cause the end effector 310 to close, as shown in FIG. 11.

Figure 12:
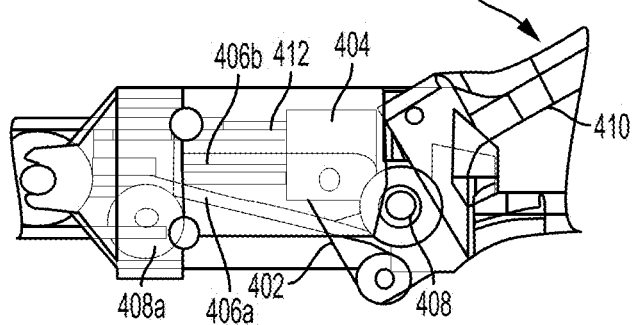
FIG. 12 is a side, partially transparent view of a portion of yet another embodiment of a surgical tool with an end effector thereof in an open position.
Figure 13:
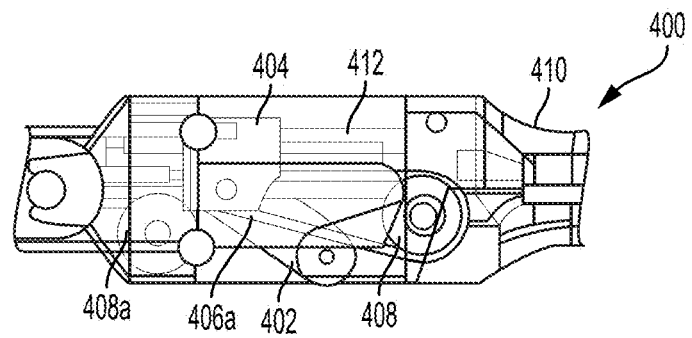
FIG. 13 is a side, partially transparent view of the portion of the tool of FIG. 12 with the end effector in a closed position.
Figure 14:
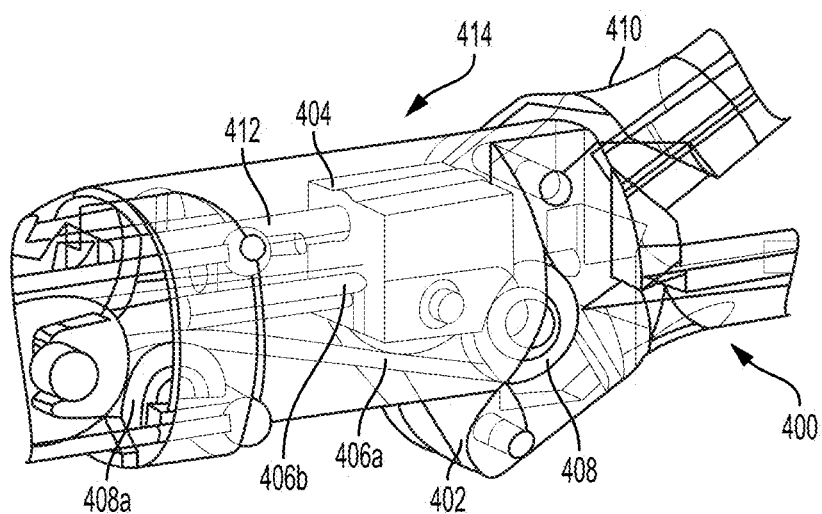
FIG. 14 is a perspective, partially transparent view of the portion of the tool of FIG. 11 with the end effector in the open position.

FIGS. 12-14 illustrate another embodiment of a surgical tool configured to apply energy to tissue. The tool of FIGS. 12-14 is configured and used similar to the tool 200 of FIGS. 6-9 except that it has a different closure mechanism than the tool 200. In the tool of FIG. 12-14, the closure mechanism configured to open and close the tool's end effector 400 includes a link 402, a slidable member 404, first and second closure cables 406a, 406b, and a pulley 408. A distal end of the link 402 is pivotally attached to the tool's upper jaw 410, and a proximal end of the link 402 is pivotally attached to the slidable member 404. The slidable member 404 is slidably attached to a support rod 412. FIGS. 12 and 14 show the end effector 400 in the open position, and FIG. 13 shows the end effector 400 in the closed position.

The first closure cable 406a is operatively coupled to the pulley 408, with the first closure cable 406a being looped around the pulley 408 with trailing ends of the closure cable 406a extending proximally from the pulley 408. The pulley 408 is located distal to the slidable member 404. A distal end of the first closure cable 406a is attached to a distal end of the slidable member 404. The tool also includes a second pulley 408a that is located proximal to the slidable member 404. The second pulley 408a is configured to help smoothly guide the first closure cable 406a into the tool's elongate shaft (not shown in FIGS. 12-14 for clarity of illustration). A proximal end of the first closure cable 406a is at the tool's tool housing and is operatively coupled to one of the tool housing's input interfaces. A distal end of the second closure cable 406b is attached to a proximal end of the slidable member 404. A proximal end of the second closure cable 406b is at the tool's tool housing and is operatively coupled to one of the tool housing's input interfaces. The first and second closure cables 406a, 406b can thus be actuated via an input from a robotic surgical system provided to the input interfaces to which the first closure cables 406a, 406b are respectively operatively coupled, e.g., an input causing the input interfaces to rotate and thereby cause longitudinal translation of their respective closure cables 406a, 406b.

In response to the actuation of the first and second closure cables 406a, 406b, the first and second closure cables 406 translate longitudinally, thereby causing the hub 404 to slide either proximally (in response to the second closure cable 406b being pulled proximally) to close the end effector 400 or distally (in response to the first closure cable 406a being pulled proximally and sliding around the pulley 408) to open the end effector 400. Since both of the closure cables 406a, 406b are attached to the hub 404, when the second closure cable 406b is pulled proximally the first closure cable 406a is pushed distally, and when the first closure cable 406a is pulled proximally the second closure cable 406b is pushed distally. In other words, the first and second closure cables 406a, 406b are configured to simultaneously move in opposite directions to effect opening/closing of the end effector 400. The input interfaces to which the first and second closure cables 406a, 406b are respectively operatively coupled are therefore configured to work in cooperation with one another, with one of the inputs to the input interfaces pulling and "winding up" one of the cables 406a, 406b and the other of the inputs to the input interfaces pushing and "letting out" the other of the cables 406a, 406b at a force substantially equal to the pulling force. A person skilled in the art will appreciate that the pushing and pulling forces may not be precisely equal but nevertheless be considered to be substantially equal due to any number of factors, such as manufacturing tolerance and precision of measurement devices. Independent movement of the first and second closure cables 406a, 406b to effect end effector opening/closing may accommodate different forces needed for each closure cable 406a, 406b due to the closure cables 406a, 406b being flexed different amounts depending on an articulation angle of the end effector 400 and/or due to the closure cables 406a, 406b experiencing different wear over time such that one of the closure cables 406a, 406b becomes more slack over time than the other of the closure cables 406a, 406b. The pulling forces to cause end effector opening and closing are less for the tool of FIGS. 12-14 than for the tool 200 of FIGS. 6-9 and the tool of FIGS. 10 and 11, which may provide for more precise control of end effector opening/closing. Each of the closure cables 406a, 406b are attached to the hub 404 in an upper half of the tool's wrist 414, which may help balance the antagonistic or opposite forces applied thereto and cause smooth movement of the link 402 during end effector 400 opening/closing.

In another embodiment, a surgical tool can be configured and used similar to the tool of FIGS. 12-14 except that the tool can include a second link in addition to the link 402, similar to the surgical tools discussed above that include a pair of links.

Figure 15:
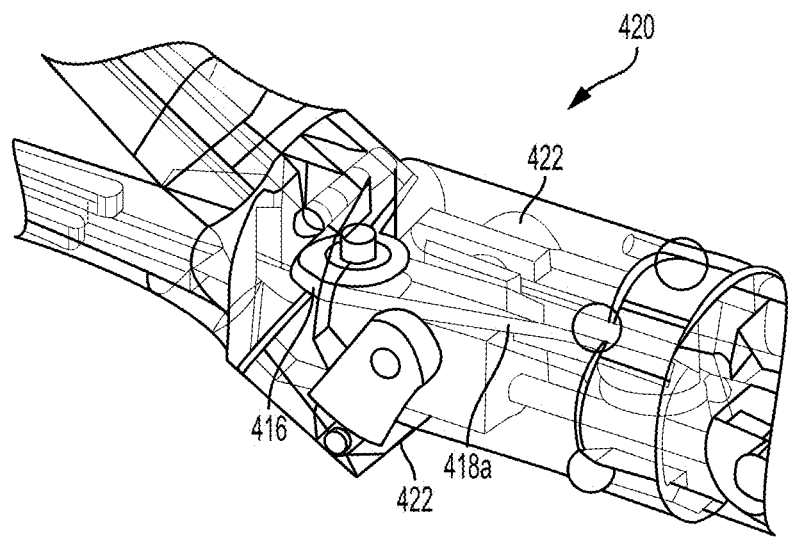
FIG. 15 is a perspective, partially transparent view of a portion of another embodiment of a surgical tool with an end effector thereof in an open position.

FIG. 15 illustrates another embodiment of a surgical tool configured to apply energy to tissue. The tool of FIG. 15 is configured and used similar to the tool of FIGS. 12-14 except that it has its pulley 416 for its first closure cable 418a at a different orientation at the tool's wrist 420 than the tool of FIGS. 12-14. The tool of FIG. 15 also has a pair of links 422, as opposed to the tool of FIGS. 12-14 that only has one link 402. In the tool of FIGS. 12-14, the pulley 408 for the first closure cable 406a is in a vertical orientation such that trailing ends of the first closure cable 406a are vertically arranged, e.g., one of the trailing ends is above the other of the trailing ends. In the tool of FIG. 15, the pulley 416 is in a horizontal orientation such that trailing ends of the first closure cable 418a are horizontally arranged, e.g., the trailing ends are laterally spaced apart from one another. The horizontal orientation of the pulley 416 may free more space at the tool's wrist 420 for the tool's articulation cables, energy cable, and ground cable.

Figure 16:
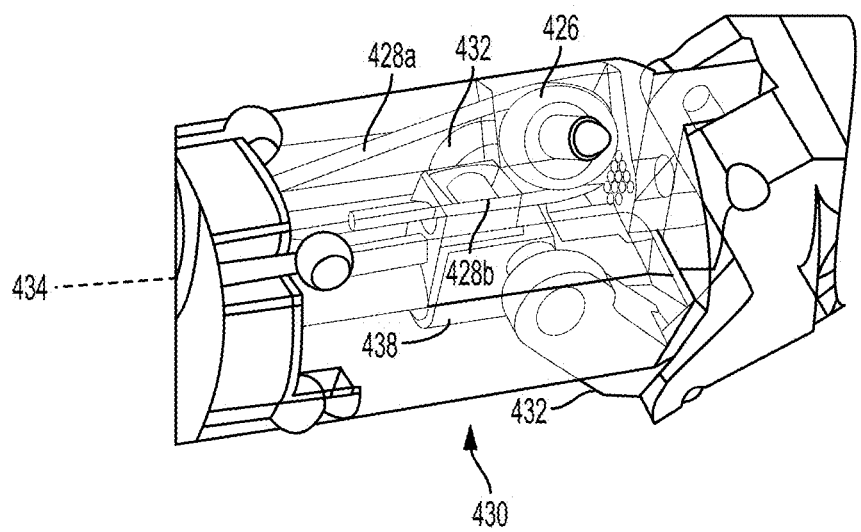
FIG. 16 is a perspective, partially transparent view of a portion of yet another embodiment of a surgical tool with an end effector thereof in an open position.
Figure 17:
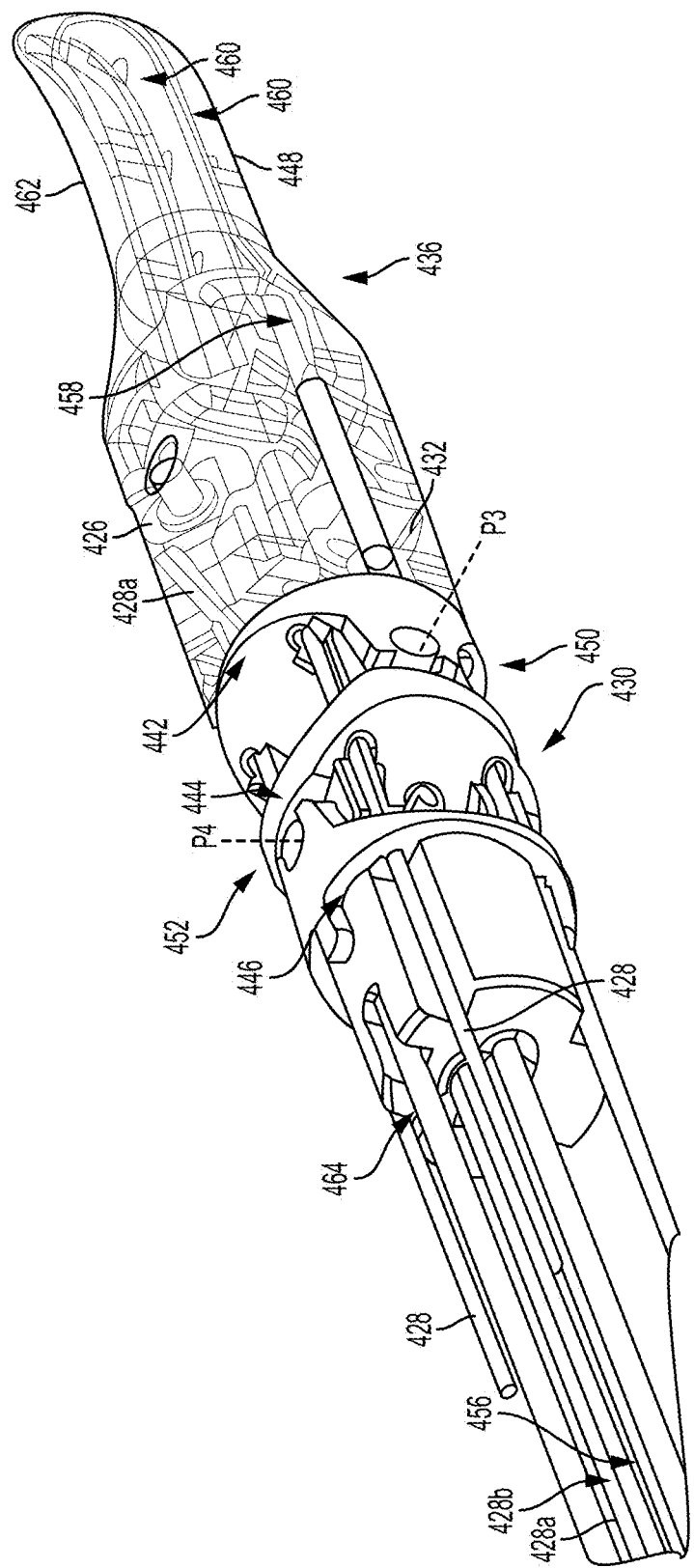
FIG. 17 is a perspective, partially transparent view of a distal portion of the tool of FIG. 16 with the end effector in a closed position.
Figure 18:
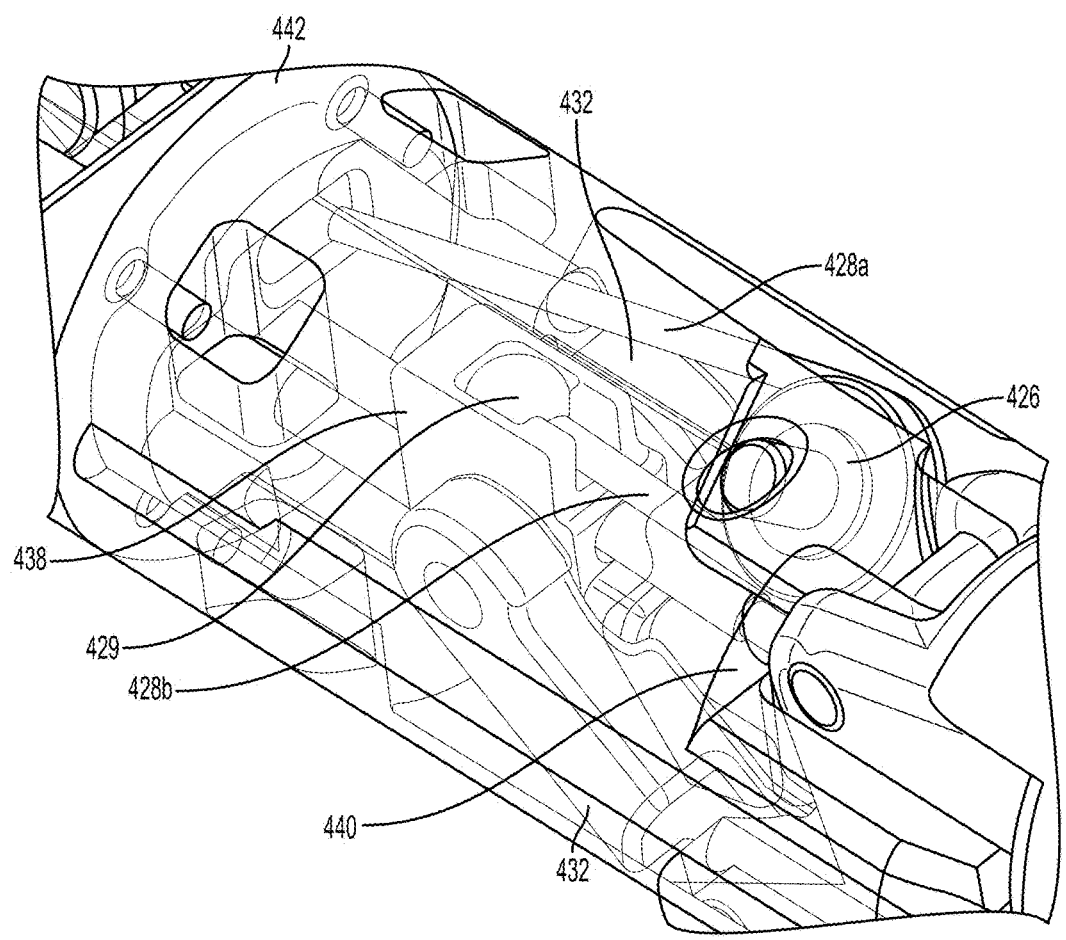
FIG. 18 is a perspective, partially transparent view of a portion of the tool of FIG. 16 with the end effector in the open position.
Figure 19:
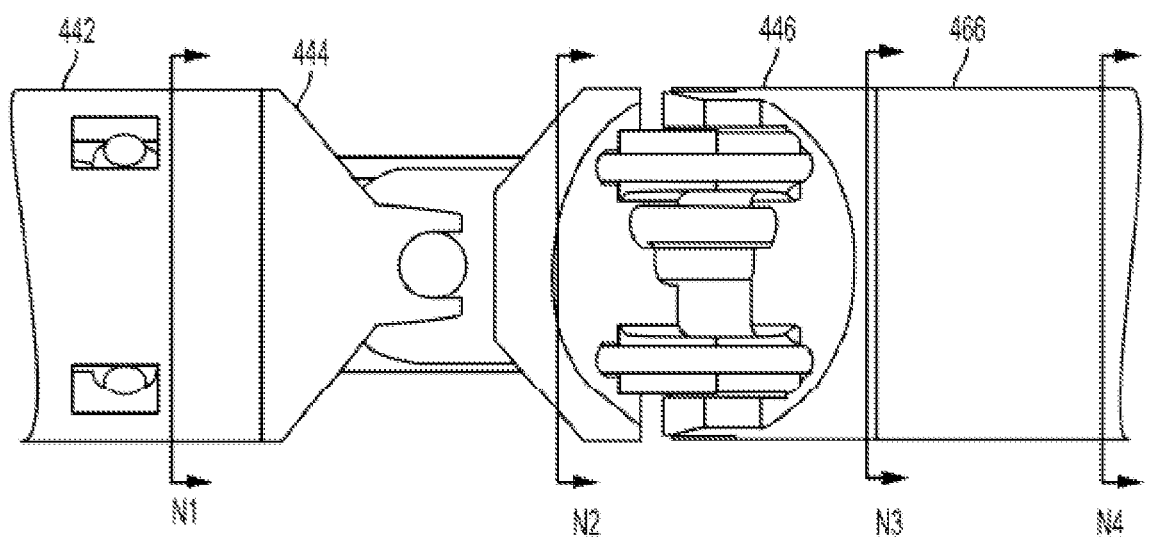
FIG. 19 is a side view of a portion of the tool of FIG. 16.

FIGS. 16-18 illustrate another embodiment of a surgical tool configured to apply energy to tissue. The tool of FIGS. 16-18 is configured and used similar to the tool of FIGS. 12-14 except that it has its pulley 426 for its first closure cable 428a at a different orientation at the tool's wrist 430 than the tool of FIGS. 12-14 and than the tool of FIG. 15. The tool of FIGS. 16-18 also has a pair of links 432, as opposed to the tool of FIGS. 12-14 that only has one link 402. In the tool of FIGS. 16-18, the pulley 426 is at an angled orientation such that trailing ends of the first closure cable 428a are angularly offset from one another, e.g., the trailing ends are laterally spaced apart from one another and are vertically offset from one another. The pulley 426 is at about a 45° angle in this illustrated embodiment, but the pulley 426 can be angularly offset at another angle. A person skilled in the art will appreciate that the angle may not be precisely at a value, e.g., precisely at 45°, but nevertheless be considered to be substantially about that value due to any number of factors, such as manufacturing tolerance and precision of measurement devices. The angled orientation of the pulley 426 may allow for the pulley 426 to have a smaller diameter (e.g., about 3 mm outer diameter) than if the pulley were arranged horizontally, e.g., as in the embodiment of FIG. 15, or arranged vertically, e.g., as in the embodiment of FIGS. 12-14. Since real estate at the wrist 430 is limited, smaller components at the wrist 430 may help accommodate all necessary components. The angled orientation of the pulley 426 still allows for the first closure cable 426a to be close to a central longitudinal axis 434 of the tool's elongate shaft 466 (see FIG. 19), similar to the embodiments of FIGS. 12-14 and FIG. 15. The first closure cable 426a and second closure cable 426b each being as close to the central longitudinal axis 434 as possible may help prevent off-axis motion of the tool's end effector 436 and/or limit the need to adjust for different closure cable lengths as the closure cables 426a, 426b as farther away radially from the central longitudinal axis 434.

As mentioned above, a distal end of a cable can be enlarged to facilitate attachment thereof to another component. FIG. 18 illustrates an enlarged distal end 429 of the second closure cable 428b that facilitates attachment of the second closure cable 428b to the tool's slidable member 438. As also shown in FIG. 18, the slidable member 438 is slidably attached to a support rod 440.

As shown in FIG. 17, the tool includes three linkages 442, 444, 446 at the wrist 430. Similar to that discussed above regarding the linkage 208 of FIGS. 6-9, the linkages 442, 444, 446 are configured to facilitate articulation of the end effector 436 relative to the elongate shaft 466. A distal end of the first linkage 442 is non-pivotally coupled to a proximal end of the end effector 436, e.g., to a proximal end of the end effector's bottom jaw 448. A proximal end of the first linkage 442 is pivotally coupled at a first or distal joint 450 to a distal end of the second linkage 444. A proximal end of the second linkage 444 is pivotally coupled at a second or proximal joint 452 to a distal end of the third linkage 446. A proximal end of the third linkage 446 is non-pivotally coupled a distal end of the elongate shaft 466.

The first joint 450 defines a first pivot axis P3 about which the first linkage 442, and hence the end effector non-pivotally coupled thereto, is configured to pivot relative to the second linkage 444 in pitch motion. The first joint 450 thus defines a first plane in which the first linkage 442, and hence the end effector, is configured to move relative to the elongate shaft 466 to adjust the end effector's pitch relative to the elongate shaft 466. The second joint 452 defines a second pivot axis P4 about which the second linkage 444 is configured to pivot relative to the third linkage 446, and hence to the elongate shaft 466 non-pivotally coupled to the third linkage 446, in yaw motion. The second joint 452 thus defines a second plane in which the second linkage 444 is configured to move relative to the third linkage 446, and hence the elongate shaft 466, to adjust the end effector's yaw relative to the elongate shaft 466. The end effector 436 is in an unarticulated position in FIGS. 16-18.

Figure 20:
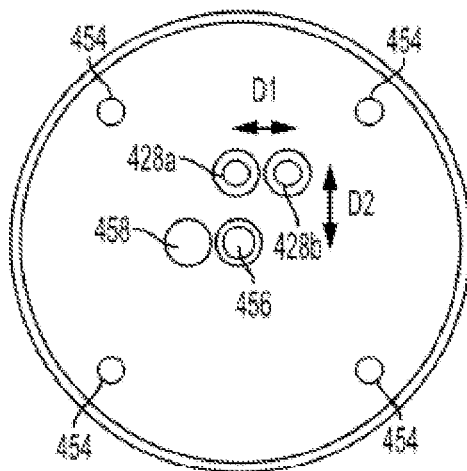
FIG. 20 is a schematic view of an arrangement of cables at a first position along the tool of FIG. 19.
Figure 21:
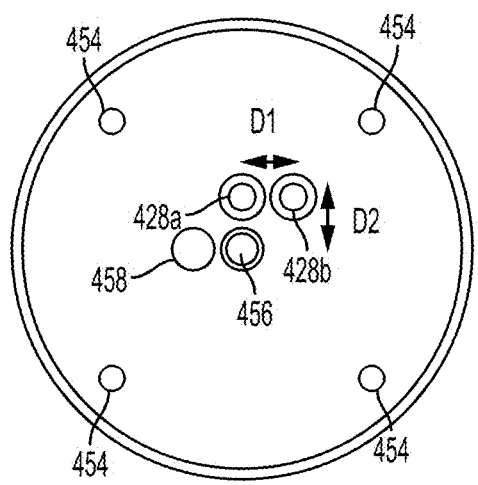
FIG. 21 is a schematic view of an arrangement of cables at second and third positions along the tool of FIG. 19.
Figure 22:
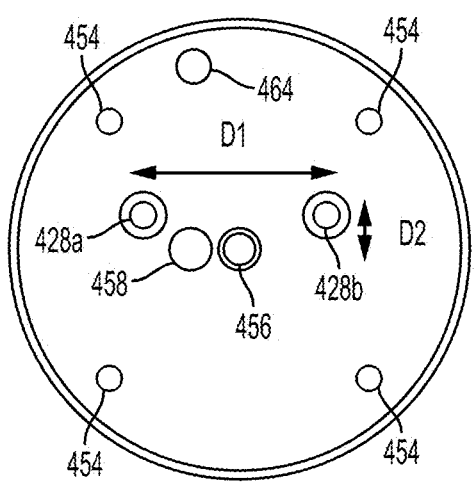
FIG. 22 is a schematic view of an arrangement of cables at a fourth position along the tool of FIG. 19.

As shown in FIGS. 17 and 20-22, the tool in this illustrated embodiment includes four articulation cables 454 (the articulation cable in the lower left is obscured in FIG. 17 but is visible in FIGS. 20-22) configured to facilitate articulation of the end effector 436, a cutting element cable 456 configured to facilitate movement of the tool's cutting element (obscured in FIGS. 16-18), an energy cable 458 configured to facilitate delivery of energy to electrodes 460 coupled to the upper and lower jaws 462, 448, and a ground cable 464. FIGS. 19-22 illustrate the positions of the closure cables 428a, 428b, the articulation cables 454, the cutting element cable 456, the energy cable 458, and the ground cable 464 at four positions N1, N2, N3, N4 longitudinally along the tool. The fourth position N4 is at a proximal end of the elongate shaft 466. The articulation cables 454, energy cable 458, and ground cable 464 are at the same location in all of the four positions N1, N2, N3, N4, e.g., are at a same distance radially from the central longitudinal axis 434 and at a same relative distance from each other. In the first position N1, as shown in FIG. 20, the first and second closure cables 428a, 428b are at a lateral or horizontal distance D1 from each other, e.g., about 9 mm, and are at a vertical distance D2, e.g., about 1.4 mm, from the central longitudinal axis 434, along which the cutting element cable 456 extends. In the second and third positions N2, N3, as shown in FIG. 21, the horizontal distance D1 is the same as in the first position N1, and the vertical distance D2 has decreased from the third position N3, e.g., decreased from about 1.4 mm to about 0.9 mm. In the fourth position N4, as shown in FIG. 22, the horizontal distance D1 has increased from the third position N3, e.g., increased from 0.9 mm to about 4.0 mm, and the vertical distance D2 has decreased from the third position N3, e.g., decreased from about 0.9 mm to about 0.3 mm. The relative positions of the first and second closure cables 428a, 428b being different at different positions longitudinally along the tool may reflect the first closure cable's angled extension from the pulley 426 and/or may help facilitate packaging and/or layout.

Figure 23:
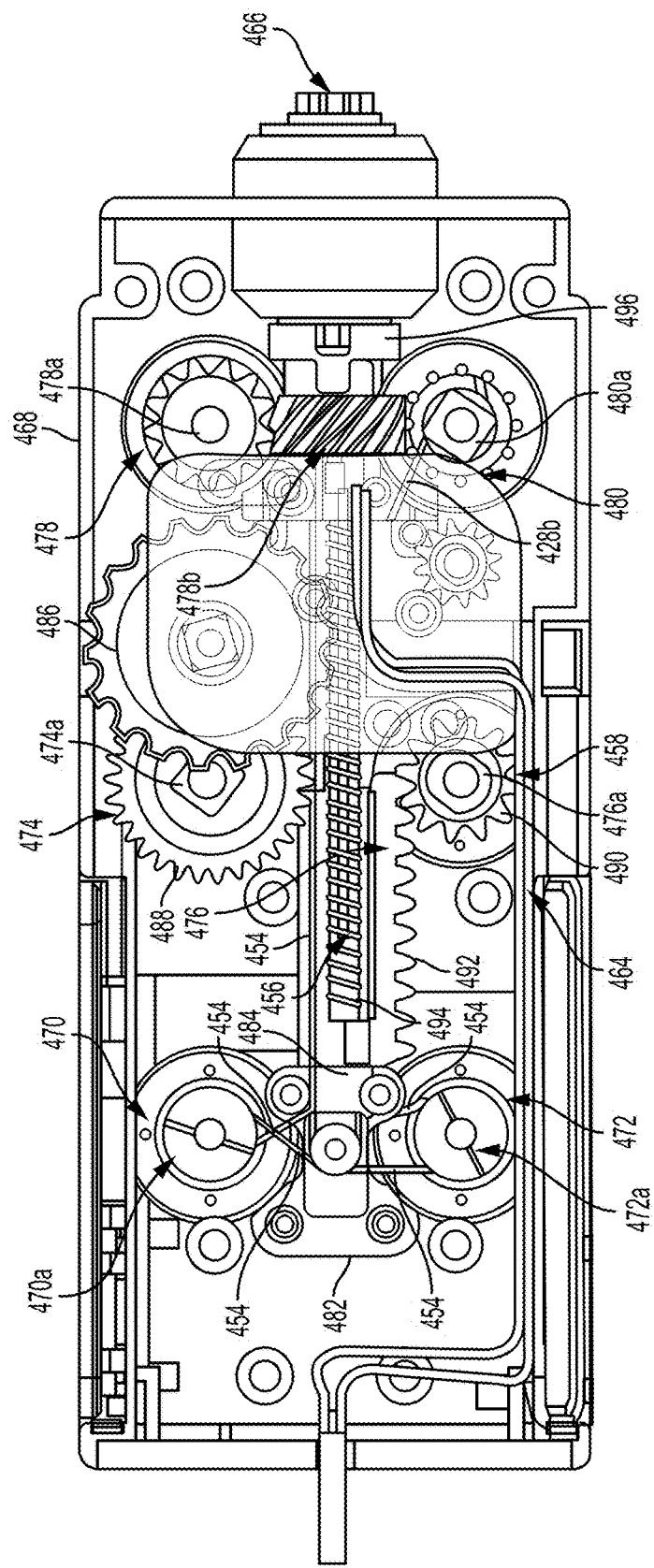
FIG. 23 is a top, partially transparent view of a tool housing of the tool of FIG. 16.
Figure 24:
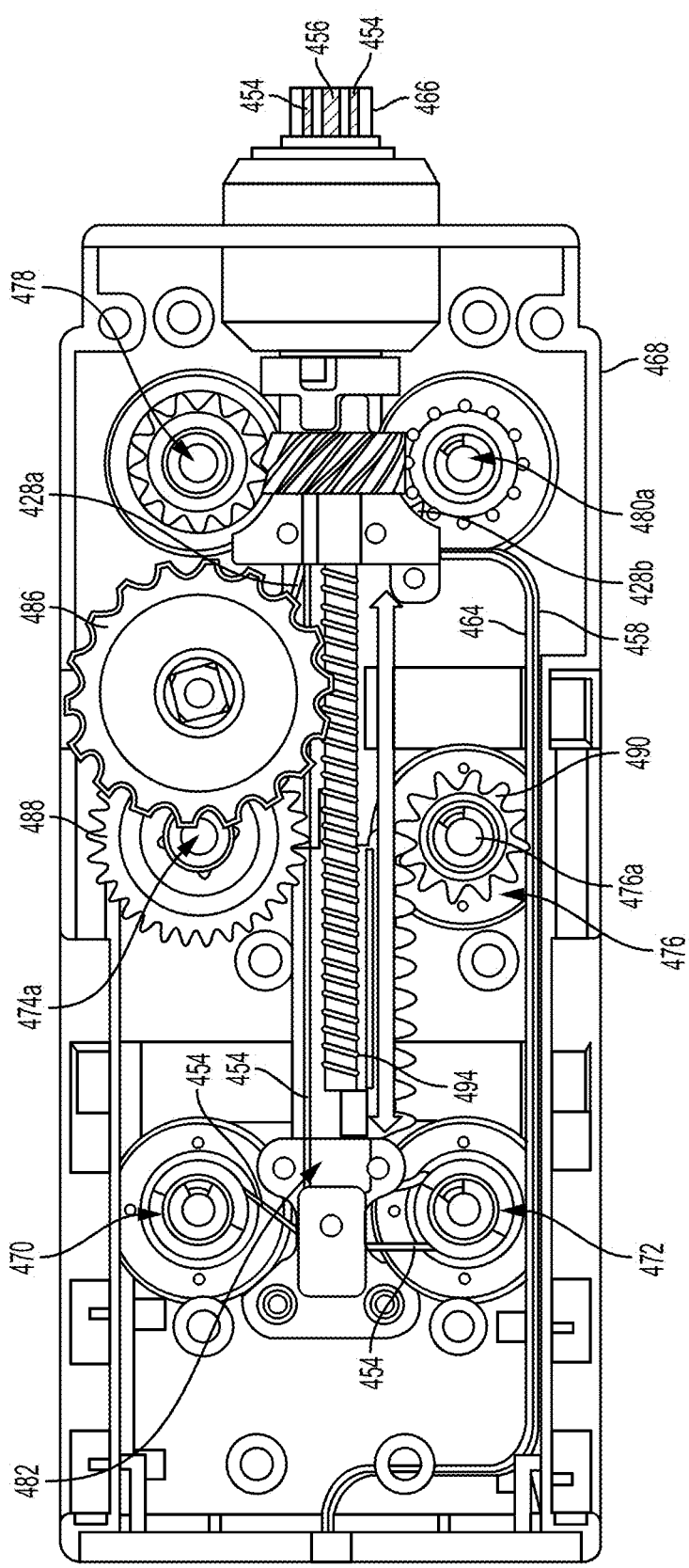
FIG. 24 is another top, partially transparent view of the tool housing of FIG. 23.
Figure 25:
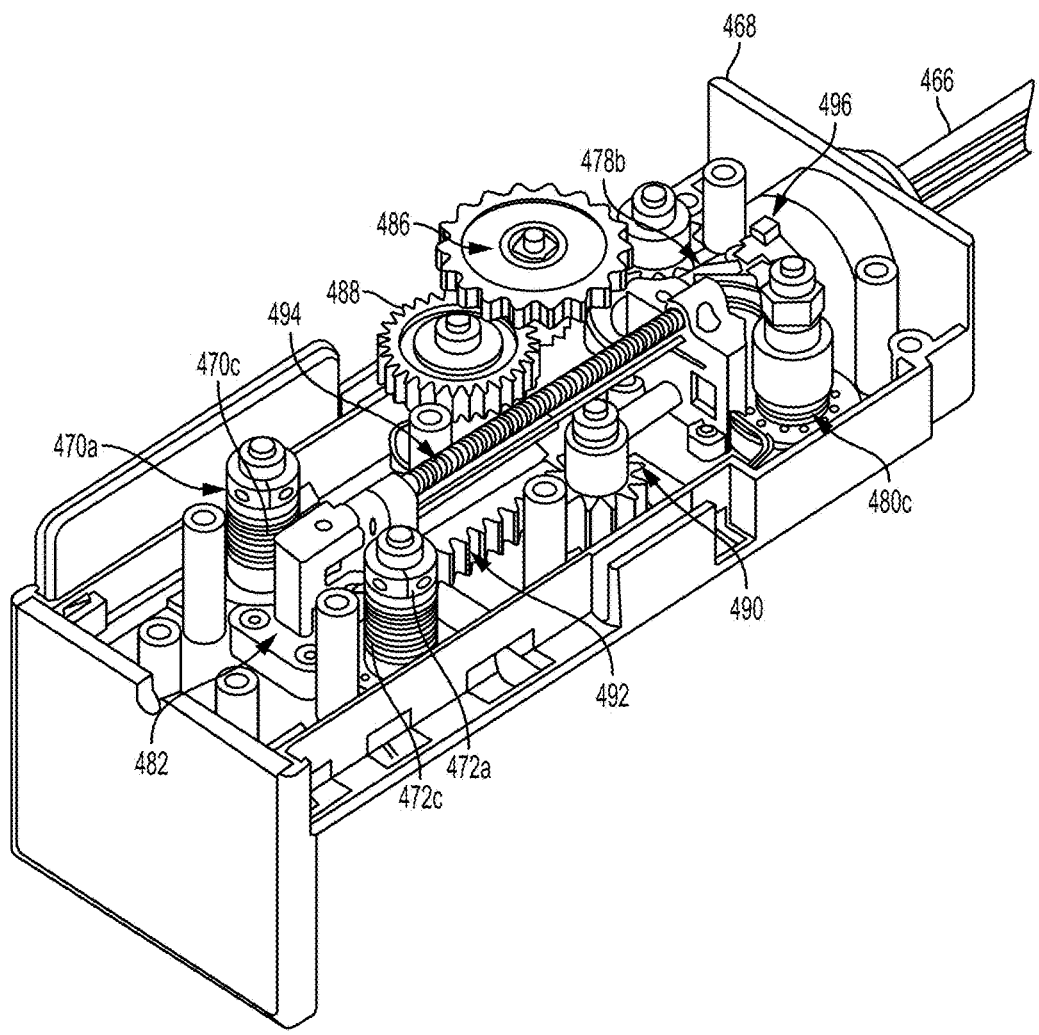
FIG. 25 is a perspective, partially cut away view of the tool housing of FIG. 23.

FIGS. 23-25 illustrate one embodiment of a tool housing 468 that can be coupled to a proximal end of the elongate shaft 466. The tool housing 468 has six input interfaces 470, 472, 474, 476, 478, 480 each configured to receive an input from a robotic surgical system (e.g., a tool driver thereof) coupled to the tool housing 468. The input interfaces 470, 472, 474, 476, 478, 480 are rotary inputs in this illustrated embodiment, e.g., each are configured to rotate to effect a function of the tool. As shown in FIG. 23, the first and second closure cables 428a, 428b, the articulation cables 454, and the cutting element cable 456 are operatively coupled to their respective input interfaces with plastic interfaces to facilitate electrical isolation. The first and second articulation cables 464 are attached to a first plastic capstan 470a, the third and fourth articulation cables 464 are attached to a second plastic capstan 472a, the first closure cable 426a is attached to a third plastic capstan 474a, the cutting element cable 456 is attached to a fourth plastic capstan 476a, and the second closure cable 426b is attached to a fifth plastic capstan 480a. The energy cable 458 and the ground cable 464 extend proximally from the housing 468 to connect to a generator (not shown).

The first input interface 470 is configured to receive an input from the robotic surgical system to drive two of the tool's four articulation cables 464 to facilitate articulation of the end effector 436. The second input interface 472 is configured to receive an input from the robotic surgical system to drive the other two of the tool's four articulation cables 464 to facilitate articulation of the end effector 436. The articulation cables 464 can be pre-tensioned at assembly at their respective input interfaces 470, 472, which may help ensure accuracy and stability. As shown in FIG. 25, the first and second input interfaces 470, 472 include the first and second capstans or winches 470a, 472b, respectively, that operatively engages the pair of articulation cables 464 associated therewith, e.g., terminal ends of the articulation cables 464 are attached to their respective winches 470b, 472b. The first winch 470a is also shown in FIGS. 26 and 27. The first input interface 470 is configured to receive an input from a first motor of the tool driver that operatively couples to the tool housing 468 that drives rotation of the first winch 470a to thereby drive longitudinal movement of the pair of articulation cables 464 operatively coupled to the first input interface 470. The input to the first input interface 470 can thus be a rotational input. Similarly, the second input interface 472 is configured to receive an input from a second motor of the tool driver that operatively couples to the tool housing 468 that drives rotation of the second winch 472a to thereby drive longitudinal movement of the pair of articulation cables 464 operatively coupled to the second input interface 472. The input to the second input interface 472 can thus be a rotational input. Each of the winches 470a, 472a can be operatively coupled to first and second bias members 470c, 472c, which in this illustrated embodiment include torsion springs coiled around their respective winches 470a, 472a. The bias members 470c, 472c are configured to bias the end effector 436 to an unarticulated position by biasing their respective winches 470b, 472 to hold their respective pair of articulation cables 464 at a tension that keeps the end effector 436 unarticulated. The end effector 436 can thus be biased to the unarticulated position, via the bias members 470c, 472c, even when the tool is not coupled to a robotic surgical system. The end effector 436 being biased to the unarticulated position may facilitate removal of the tool from a trocar or other access device.

The tool housing 468 in this illustrated embodiment includes a routing and support member 482 configured to route the articulation cables 464 therethrough to their associated one of the first and second input interfaces 470, 472. The routing and support member 482 is also configured to support a rod 484 operatively coupled to the cutting element cable 456.

The third input interface 474 and the sixth input interface 480 are each configured to receive an input from the robotic surgical system to drive selective end effector 436 opening and closing. The input to the third input interface 474 is configured to cause rotation of the third capstan 474a that is operatively engaged with the first closure cable 428a. The input to the third input interface 474 can thus be a rotational input. The rotation of the third capstan 474a is configured to cause longitudinal translation of the first closure cable 428a.

Similarly, the input to the sixth input interface 480 is configured to cause rotation of the sixth capstan 480a that is operatively engaged with the second closure cable 428b. The input to the sixth input interface 480 can thus be a rotational input. The rotation of the sixth capstan 480a is configured to cause longitudinal translation of the second closure cable 428b. As discussed above, the first closure cable 428a being pulled proximally and the second closure cable 428b being pushed distally will cause the end effector 436 to open, and the first closure cable 428a being pushed distally and the second closure cable 428b being pulled proximally will cause the end effector 436 to close. In other words, for end effector 436 opening the third motor operatively coupled to the third input interface 474 can be the driving motor and the sixth motor operatively coupled to the sixth motor interface 480 can be the follower motor, and for end effector 436 closing the third motor operatively coupled to the third input interface 474 can be the follower motor and the sixth motor operatively coupled to the sixth motor interface 480 can be the driving motor.

Each of the third and sixth winches 474a, 480a can be operatively coupled to first and second bias members 480c (the first bias member coupled to the third winch 474a and obscured in the figures), which in this illustrated embodiment include torsion springs coiled around their respective winches 474a, 480a. The first and second bias members 480c are configured to bias the end effector 436 to a closed position by biasing their respective winches 474a, 480a to hold their respective closure cables 428a, 428b at a tension that keeps the end effector 436 closed. The end effector 436 can thus be biased closed, via the first and second bias members 480c, even when the tool is not coupled to a robotic surgical system. The end effector 436 being biased to the closed position may facilitate removal of the tool from a trocar or other access device.

The tool housing 468 includes a manual override knob 486 configured to allow for manual opening and closing of the end effector 436. The manual override knob 486 is accessible from outside the tool housing 468, e.g., accessible to be manually moved by hand from outside the tool housing 468. The manual override knob 486 may allow end effector 436 opening/closing in the unlikely event of power failure that prevents end effector 436 opening/closing via input to the third and sixth input interfaces 474, 480. Rotating the manual override knob 486 in one direction will cause the end effector 436 to open by rotating a corresponding gear 488 coupled to the third winch 474a, and rotating the manual override knob 486 in the other direction will cause the end effector 436 to close by rotating the corresponding gear 488 coupled to the third winch 474a. The manual override knob 486 can have other configurations, such as levers, actuators, arms, and triggers, to rotate the corresponding gear 488 and cause manual override.

The fourth input interface 476 is configured to receive an input from the robotic surgical system to drive cutting element translation via a rack and pinion system that is operatively coupled to the cutting element cable 456. The input to the fourth input interface 476 is configured to cause rotation of a pinion 490 that is operatively engaged with a rack 492, which is operatively coupled to the rod 484. The input to the fourth input interface 476 can thus be a rotational input. The rack 492 is operatively coupled with the cutting element cable 436 via the rod 484 such that the translational movement of the rack 492 causes corresponding translational movement of the cutting element cable 436, thereby causing selective translation of the cutting element proximally (proximal translation of the rack 492, and rotation of the pinion 490 in one direction) or distally (distal translation of the rack 492, and rotation of the pinion 490 in an opposite direction).

The tool housing 468 includes a bias element 494 configured to bias the cutting element to a distal position, which may help prevent the cutting element from accidentally cutting tissue and/or other material between the jaws of the end effector 436. The bias element 494 in this illustrated embodiment is a spring coiled around the rod 484. A distal end of the bias element 494 abuts a second routing and support member 498, and a proximal end of the bias element abut an extension of the rack 292. The second routing and support member 498 is configured to route the closure cables 428a, 428b therethrough to their respective input interfaces 474, 480, to route the cutting element cable 456 to the fourth input interface 476, and to support the rod 484.

The fifth input interface 478 is configured to receive an input from the robotic surgical system to drive rotation of the elongate shaft 466 via a gear system. The input to the fifth input interface 478 is configured to cause rotation of a first gear 478a. The input to the fifth input interface 478 can thus be a rotational input. The rotation of the first gear 478a is configured to rotate a second gear 478b operatively engaged therewith. The second gear 478b is operatively coupled to the shaft 466 such that rotation of the second gear 478b rotates the elongate shaft 466 (and the end effector 436 at the distal end thereof). The tool housing includes a stop member 496 configured to prevent rotation of the shaft 466 beyond about 540°, e.g., is configured to allow free rotation of the shaft 466 up to about 540°.

FIG. 28 illustrates another embodiment of a tool housing 700 that can be coupled to a proximal end of an elongate shaft of a surgical tool configured to apply energy to tissue. In this illustrated embodiment, first and second bias members 702, 704, which are in the form of constant force springs, are configured to bias the tool's end effector (not shown) to an unarticulated position by holding their respective associated pair of articulation cables (not shown) at a tension that keeps the end effector unarticulated. The bias members 702, 704 are generally configured and used similar to the first and second bias members 470c, 472c discussed above. FIG. 28 illustrates a distal direction R1 of the force applied by the bias members 702, 704 and a proximal direction R2 of the force applied to push the articulation cables. As shown, the bias members 702, 704 are located at a distal end of the tool housing 700, which allows the bias members 702, 704 to provide forces in the appropriate direction without the need for any pulleys to redirect the forces. FIG. 28 also illustrates a rack and pinion system 706 configured to effect movement of the articulation cables, similar to the rack and pinion system discussed above. The tool housing 700 can include other features to effect other functions, similar to the tool housings discussed above, e.g., shaft rotation, end effector opening/closing, etc. In at least some embodiments, the tool housing can include an amplification mechanism (e.g., a lever, etc.) configured to amplify a weaker bias member up to the required force.

Figure 29:
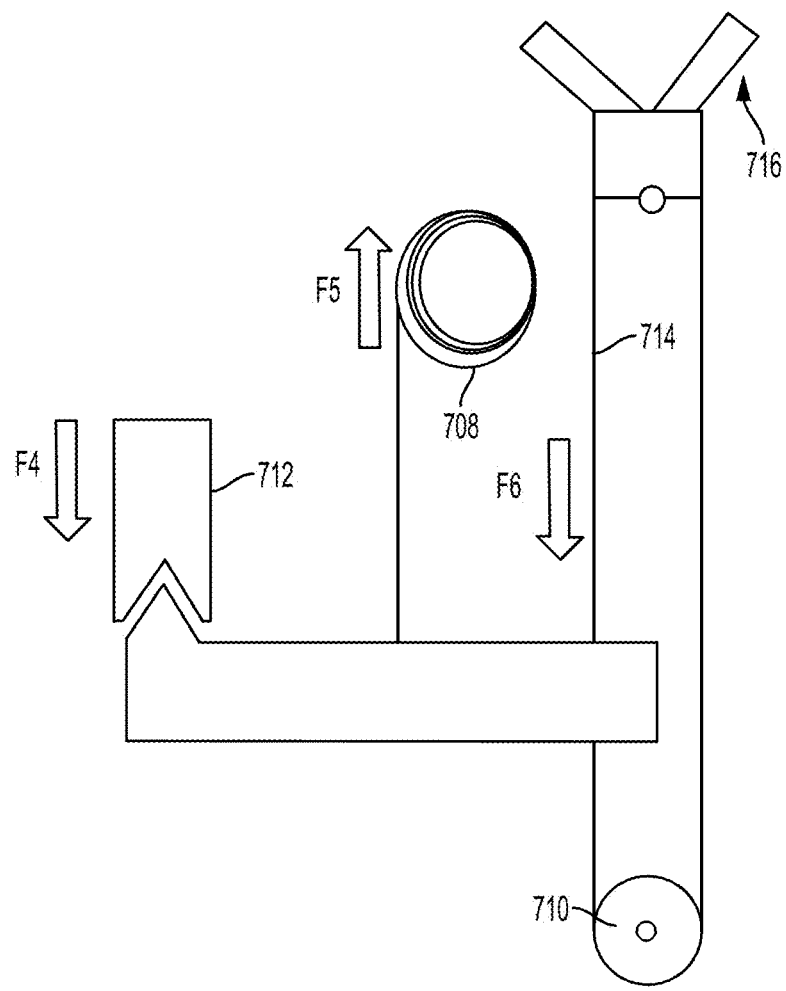
FIG. 29 is a schematic, partial view of another embodiment of a surgical tool.

In an alternate embodiment, first and second bias members can be located at a proximal end of the tool housing with a pulley included for each of the bias members to redirect their forces in the appropriate distal direction R1. The bias members being located at the tool housing's proximal end may allow for the bias members to be larger and provide more force. FIG. 29 illustrates one embodiment of a tool housing with proximally located bias members, although only one of the bias members 708 and its associated pulley 710 is shown for clarity of illustration. For example, a force F4 can be provided by the tool's actuator 712, e.g., the tool's input interface, and the bias member 708 can be configured to provide a force F5 in the opposite direction of the force F4, with an effective force F6 on the bias member's associated articulation cable 714 in both directions. About 10 mm of articulation cable travel can be needed to fully articulate the tool's end effector 716.

Figure 30:
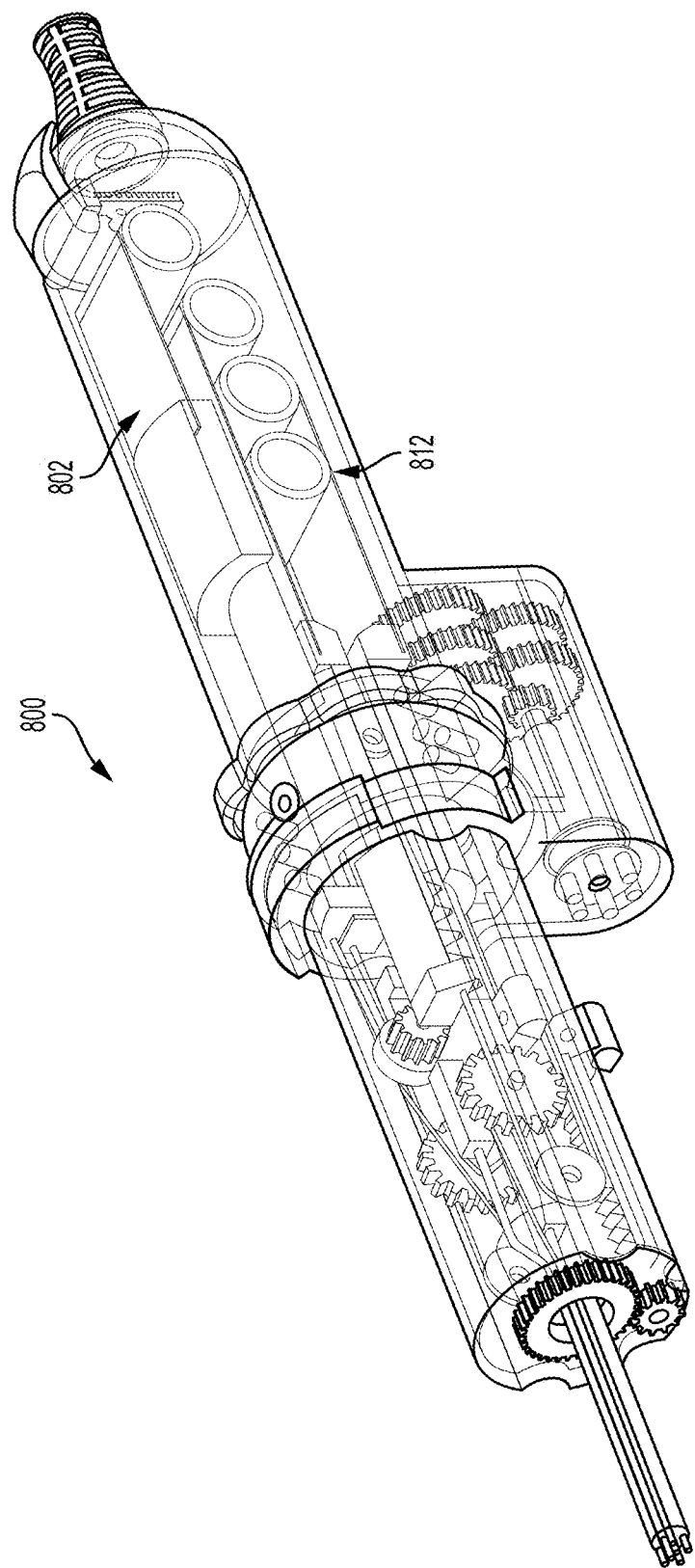
FIG. 30 is a perspective, partially transparent view of a proximal portion of still another embodiment of a surgical tool.

FIG. 30 illustrates another embodiment of a tool housing 800 that can be coupled to a proximal end of an elongate shaft of a surgical tool configured to apply energy to tissue. In this illustrated embodiment, the tool housing 800 has an extended proximal portion 802 configured to house therein bias members associated with various input interfaces of the tool housing 800, as discussed further below. In this illustrated embodiment, the tool housing 800 has six input interfaces with first and second input interfaces for articulation of the tool's end effector, a third input interface for end effector opening/closing, a fourth input interface for cutting element translation, a fifth input interface for rotation of the tool's elongate shaft, and a sixth input interface is available for other use. In this illustrated embodiment, the first and second input interfaces are rotary mechanisms, and the third, fourth, fifth, and sixth input interfaces are linear mechanisms.

Figure 31:
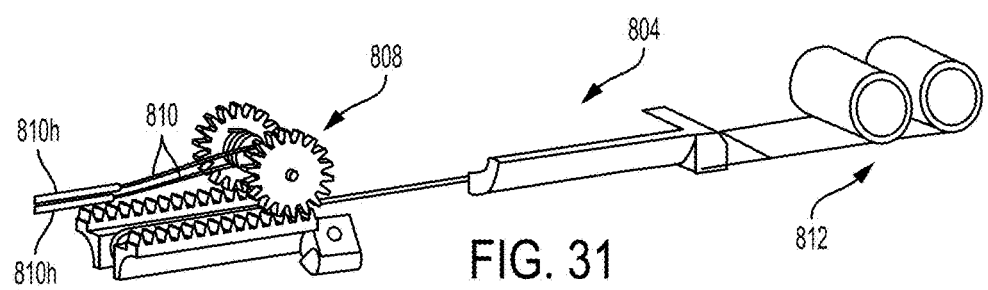
FIG. 31 is a perspective view of a first articulation mechanism of the tool of FIG. 30.
Figure 32:
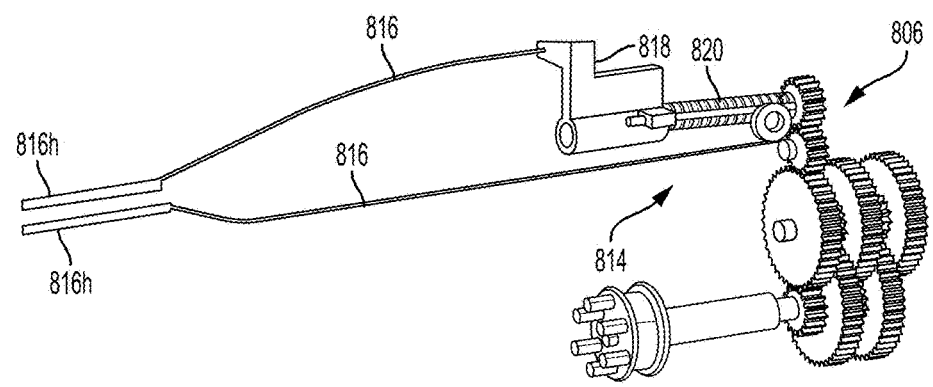
FIG. 32 is a perspective view of a second articulation mechanism of the tool of FIG. 30.

As shown in FIGS. 30-32, the first input interface for articulation includes a first articulation mechanism 804, and the second input interface for articulation includes a second articulation mechanism 806. The first articulation mechanism 804 includes a rack and pinion system 808 configured to effect articulation cable movement of a first pair articulation cables 810, similar to the rack and pinion system discussed above. The first articulation mechanism 804 also includes a pair of bias members 812, which is in the form of constant force springs in this illustrated embodiment. The second articulation mechanism 806 includes a gear system 814 configured to effect articulation cable movement of a second pair of articulation cables 816 via gear rotation that causes longitudinal translation of a translation member 818 biased with a bias member 820, which is in the form of a coil spring in this illustrated embodiment. Sensitivity of the second articulation mechanism 806 can be adjusted by changing the gearing and lead screw pitch. The first and second articulation mechanisms 804, 806 can each be configured, for example, to provide about 10 mm of translational articulation cable movement, which can be enough to cause full articulation of the end effector (e.g., +/- about 160°) and to resist a side load at the end effector's distal tip. FIGS. 31 and 32 also show hypotubes 810*h*, 816*h* containing distal portions of the articulation cables 810, 816.

Figure 34:
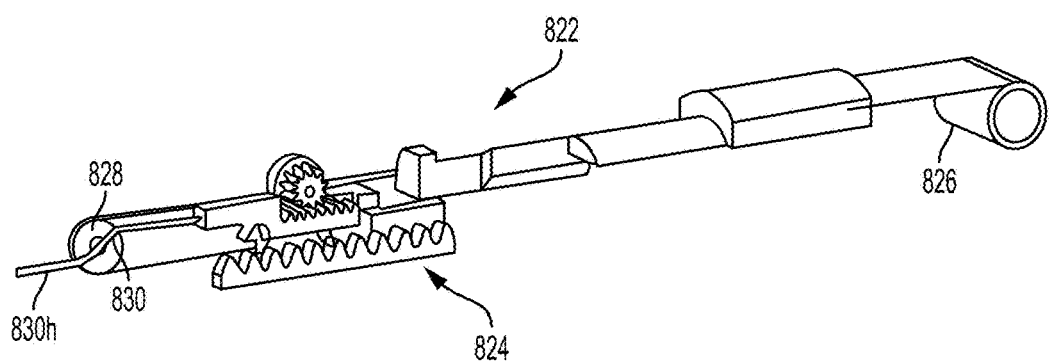
FIG. 34 is a perspective view of a closure mechanism of the tool of FIG. 30.

As shown in FIGS. 30 and 34, the third input interface can include a closure mechanism 822 that includes a rack and pinion system 824 configured to effect end effector opening/closing, similar to the rack and pinion system discussed above. The closure mechanism 822 also includes a bias element 826, which is in the form of a constant force spring in this illustrated embodiment, and a pulley 828 to direct motion in the appropriate distal direction. The closure mechanism 822 can be configured, for example, to provide about 5 mm of translational closure cable 828 movement to fully open/close the end effector (e.g., with the end effector's jaws at an angle of about 30°) and enough force to achieve clamping force at the end effector's distal tip. One input interface is used for end effector opening/closing in this illustrated embodiment since it may provide enough force to achieve the clamping force at the end effector's distal tip to effectively clamp tissue between the end effector's jaws.

FIG. 34 also shows a hypotube 830*h* containing a distal portion of the closure cable 830.

Figure 33:
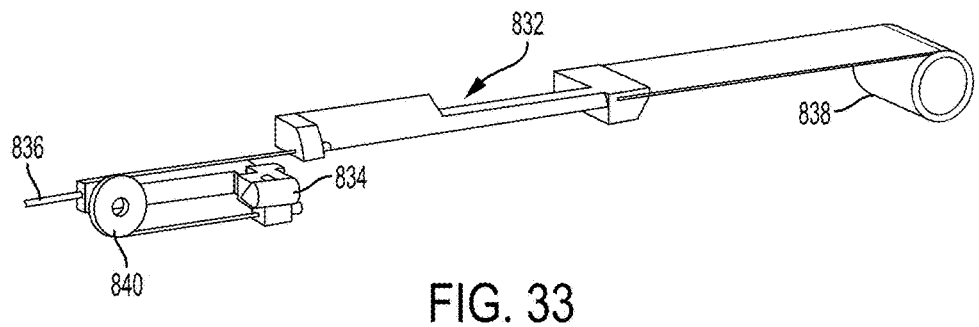
FIG. 33 is a perspective view of a cutting element translation mechanism of the tool of FIG. 30.

As shown in FIGS. 30 and 33, the fourth input interface can include a cutting element translation mechanism 832 that includes a translational member 834 configured to longitudinally translate to effect longitudinal translational movement of the cutting element cable 836. The cutting element translation mechanism 832 also includes a bias element 838, which is in the form of a constant force spring in this illustrated embodiment, and a pulley 840 to direct motion in the appropriate distal direction. The cutting element translation mechanism 832 can be configured, for example, to provide about 24 mm of cutting element translational movement to fully translate the cutting element fully along the end effector and enough force to overcome friction when the end effector is fully articulated.

Figure 35:
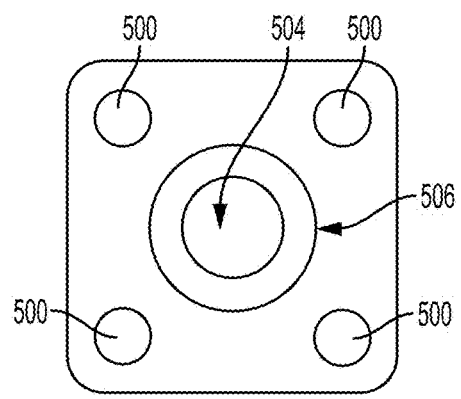
FIG. 35 is a schematic cross-sectional view of another embodiment of a surgical tool.

FIGS. 35-37 illustrate another embodiment of a surgical tool configured to apply energy to tissue. The tool of FIGS. 35-37 is generally configured and used similar to the tool of FIGS. 16-18. In this illustrated embodiment, the tool includes four articulation cables 500 arranged radially around a central longitudinal axis 502, a cutting element cable 504 extending substantially along the central longitudinal axis 502, and a jaw closure tube 506 coaxially arranged around the cutting element cable 504. The tool of FIGS. 35-37 thus does not include any closure cables, instead being configured to open and close jaws of its end effector via translational movement of the jaw closure tube 506. The cutting element cable 504 and the jaw closure tube 506 are configured to be actuated via push/pull motion (e.g., push/pull the cutting element cable 504 to cause cutting element movement, and push/pull the jaw closure tube 506 to cause jaw opening/closing) and to be freely slidable throughout the end effector's range of articulation, including when the tool's end effector is fully articulated, without buckling. The cutting element cable 504 and the jaw closure tube 506 are arranged around the central longitudinal axis 502 such that their respective actuation forces will be directed along the tool's centerline, which may help prevent the buckling and/or allow for even force distribution.

As shown in FIGS. 36 and 37, bending radii may be maximized with the cable arrangement of this illustrated embodiment. FIG. 36 shows a diameter 506*d*, e.g., about 0.95 mm, of the jaw closure tube 206, a diameter 504*d*, e.g., about 0.58 mm, of the cutting element cable 504, and a diameter 508*d*, e.g., about 5.4 mm, of a third linkage 508. The tool also has first and second linkages 510, 512. FIG. 36 also shows a hypotube 514 around the jaw closure tube 506 and the cutting element cable 504. The hypotube 514 has a diameter 514*d* of, e.g., about 2.0 mm. FIG. 36 also shows a bending radius 504*b* of the cutting element cable 504, e.g., about 5.1 mm, and a bending radius 514*b* of the hypotube 514, e.g., about 4.1 mm. The bending radii 504*b*, 514*b* can be increased by opening up a wall 508*w* of the third linkage 508. The hypotube 514, and hence also the jaw closure tube 506 and cutting element cable 504 contained therein, is configured to shift off the central longitudinal axis 502 to allow for more generous radii 504*b*, 514*b*.

Figure 40:
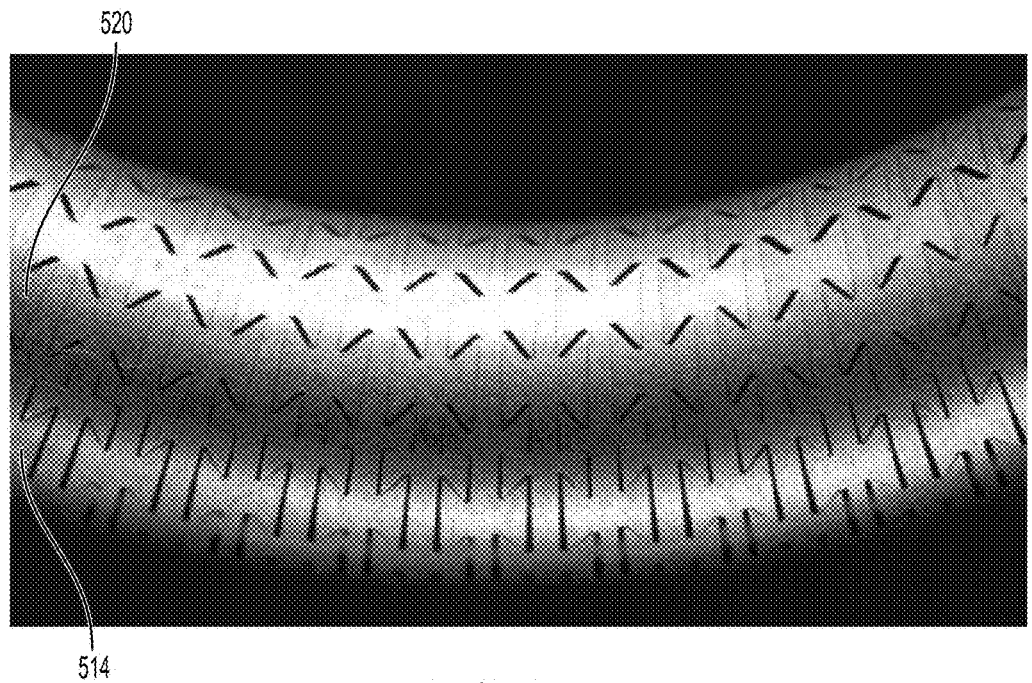
FIG. 40 is a perspective view of a portion of yet another embodiment of a hypotube.

To facilitate bending of the jaw closure tube 506 and cutting element cable 504 when the end effector is articulated, the hypotube 514 can include a plurality of cuts therein, such as by being laser cut therein. FIG. 38 illustrates one embodiment of the hypotube 514 including a plurality of cuts 516 therein that are in a spiral pattern with a pitch of about 0.35 mm. FIG. 39 illustrates another embodiment of the hypotube 514 including a plurality of cuts 518 therein that are in a spiral pattern with a pitch of about 0.20 mm. As pitch of the cuts decrease, the bending radius 514b of the hypotube 514 increases and the segments of the hypotube 514 between cuts is thinner and weaker. FIG. 40 illustrates another embodiment of the hypotube 514 including a plurality of cuts 520 therein that are in a trapezoidal pattern. In the trapezoidal pattern, each kerf cut refers to a full circumferential cut with alternate trapezoidal orientations, thereby resulting in individual segments that are interlocked axially. Increasing the number of kerf cuts in the pattern results in a smaller bend radius. A hypotube with a trapezoidal pattern of cuts is able to support a higher axial load than a hypotube with a spiral pattern of cuts.

Figure 41:
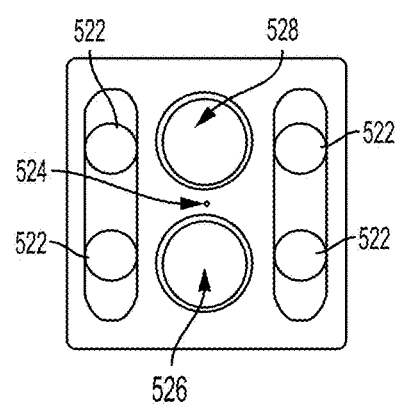
FIG. 41 is a schematic cross-sectional view of still another embodiment of a surgical tool.

FIG. 41 illustrates another embodiment of a surgical tool configured to apply energy to tissue. The tool of FIG. 41 is generally configured and used similar to the tool of FIGS. 16-18. In this illustrated embodiment, the tool includes four articulation cables 522 arranged radially around a central longitudinal axis 524, a cutting element cable 526 extending substantially parallel to and below the central longitudinal axis 524, and a closure cable 528 extending substantially parallel to and above the central longitudinal axis 524. The off-center position of the closure cable 528 creates a moment or force at the tool's wrist joints. The articulation cables 522 are configured to resist the moment or force.

Figure 42:
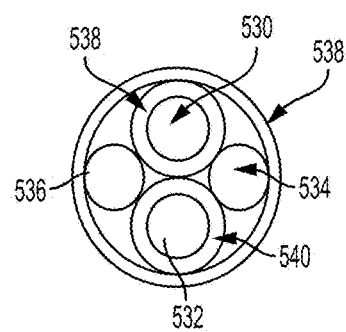
FIG. 42 is a schematic cross-sectional view of yet another embodiment of a surgical tool.

FIG. 42 illustrates another embodiment of a surgical tool configured to apply energy to tissue. The tool of FIG. 42 is generally configured and used similar to the tool of FIGS. 16-18. In this illustrated embodiment, the tool includes a closure cable 530, a cutting element cable 532, an energy cable 534, and a ground cable 536 that are each disposed in and extend through a tube 538. The tube 538 may help protect the closure cable 530, the cutting element cable 532, the energy cable 534, and the ground cable 536. The closure cable 530 and the cutting element cable 532 are also each contained in polymide braided tubing 538, 540, which may also help protect their respective cables 530, 532. Initially, as shown in FIG. 42, the tube 538 can be heat shrinked around the closure cable 530, cutting element cable 532, energy cable 534, and ground cable 536. The heat shrinking of the tube 538 can cause the closure cable 530, cutting element cable 532, energy cable 534, and ground cable 536 to abut one another, as shown in FIG. 42. In the heat shrinked tube 538, the closure cable 530, cutting element cable 532, energy cable 534, and ground cable 536 are each offset from the central longitudinal axis and are arranged therearound. The tube heat shrinked 538 can be fit to the tool, and energy cable 534 and ground cable 536 can be moved outward from their position in FIG. 42 while the cutting element cable 532 slides therebetween to extend substantially along the central longitudinal axis. This movement of the cables 532, 534, 536, and movement of the closure cable 530 that may also occur during this transition, may be gentle enough that it can occur with minimal impact on the cables.

Figure 43:
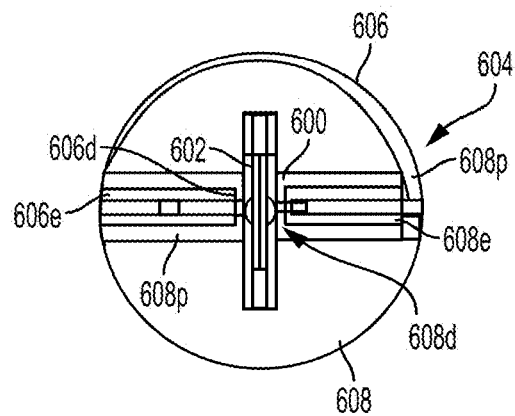
FIG. 43 is a cross-sectional view of another embodiment of a surgical tool.

In at least some embodiments of a surgical tool configured to apply energy to tissue, as discussed herein, a cutting element cable is attached to a cutting element, e.g., via welding, crimping, etc., to effect translational movement of the cutting element along an end effector of the tool. As shown in one embodiment of such a surgical tool illustrated in FIG. 43, a cutting element cable 600 is attached to a cutting element 602 that translates along the tool's end effector 604, which includes upper and lower jaws 606, 608. Each of the upper and lower jaws 606, 608 has a longitudinal slot 606s, 608s formed therein through which the cutting element 602 translates. Each of the upper and lower jaws 606, 608 also has an electrode 606e, 608e on a tissue engaging surface thereof. Edges 606d, 608d of pads 606p, 608p of the electrodes 606e, 608e are chamfered on each side of the cutting element 602, as shown in FIG. 43, to cradle the cutting element cable 600 during the translation of the cutting element 600, since the cutting element cable 600 is wider than the cutting element 602, as also shown in FIG. 43.

Figure 44:
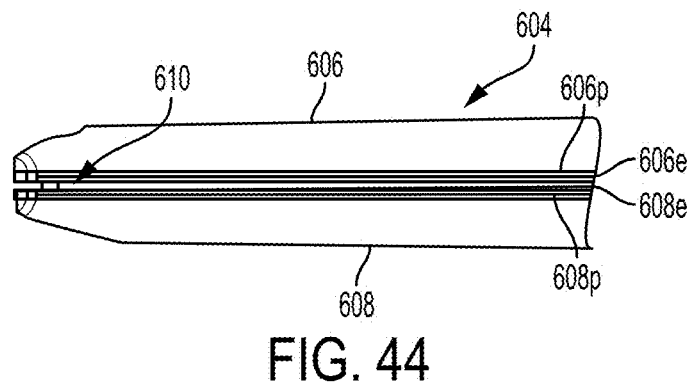
FIG. 44 is a side view of a distal portion of the tool of FIG. 43.
Figure 44A:
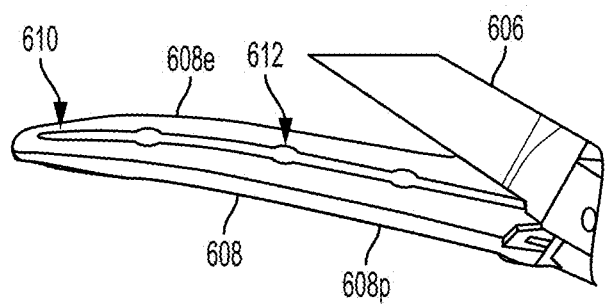
FIG. 44A is a perspective view of a portion of the tool of FIG. 43.

In at least some embodiments of a surgical tool configured to apply energy to tissue, as discussed herein, an end effector includes one or more spacers configured to ensure that a gap of space exists between the tissue contacting surfaces of the end effector's upper and lower jaws, which may help prevent shorting of electrodes on the tissue contacting surfaces. As shown in FIGS. 43-44A, one embodiment of such an end effector 604 includes a single spacer 610 at a distal end of a longitudinal slot 612 through which the cutting element 602 translates along the end effector 604. The cutting element 604 thus does not pass any spacers during its longitudinal translation along the end effector 604 while moving in the slot 612 and cutting tissue engaged by the jaws 606, 608, which may prevent the cutting element 602 and the cutting element cable 600, which is wider than the cutting element 602, from catching on the attachment point(s), e.g., weld point(s) between the cutting element 602 and the cutting element cable 600. The spacer 610 is on the lower jaw 608 and extends toward the upper jaw 606 in this illustrated embodiment, but the spacer can instead be on the upper jaw 606 and extend toward the lower jaw 608.

Figure 45:
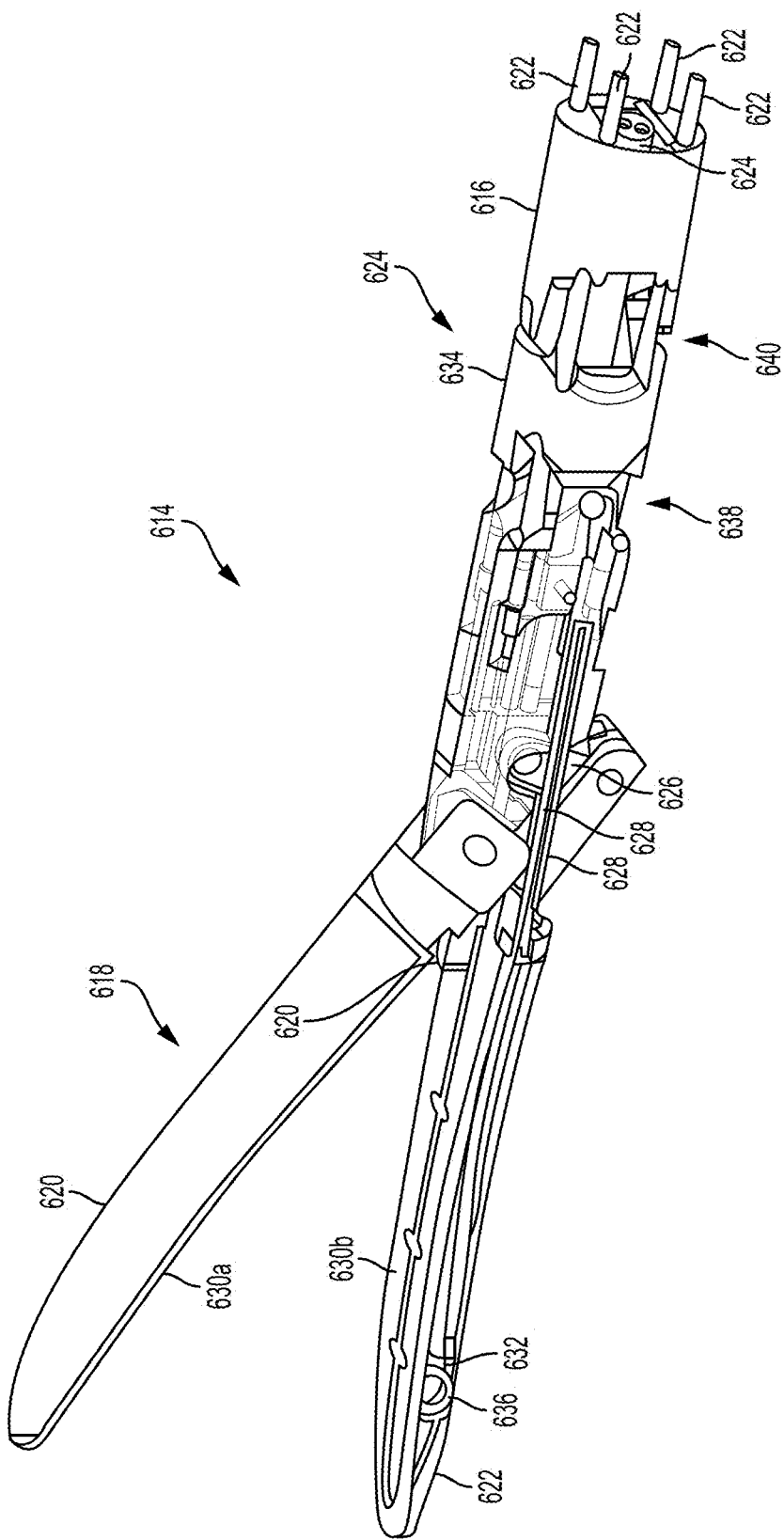
FIG. 45 is a perspective view of a distal portion of another embodiment of a surgical tool.
Figure 46:
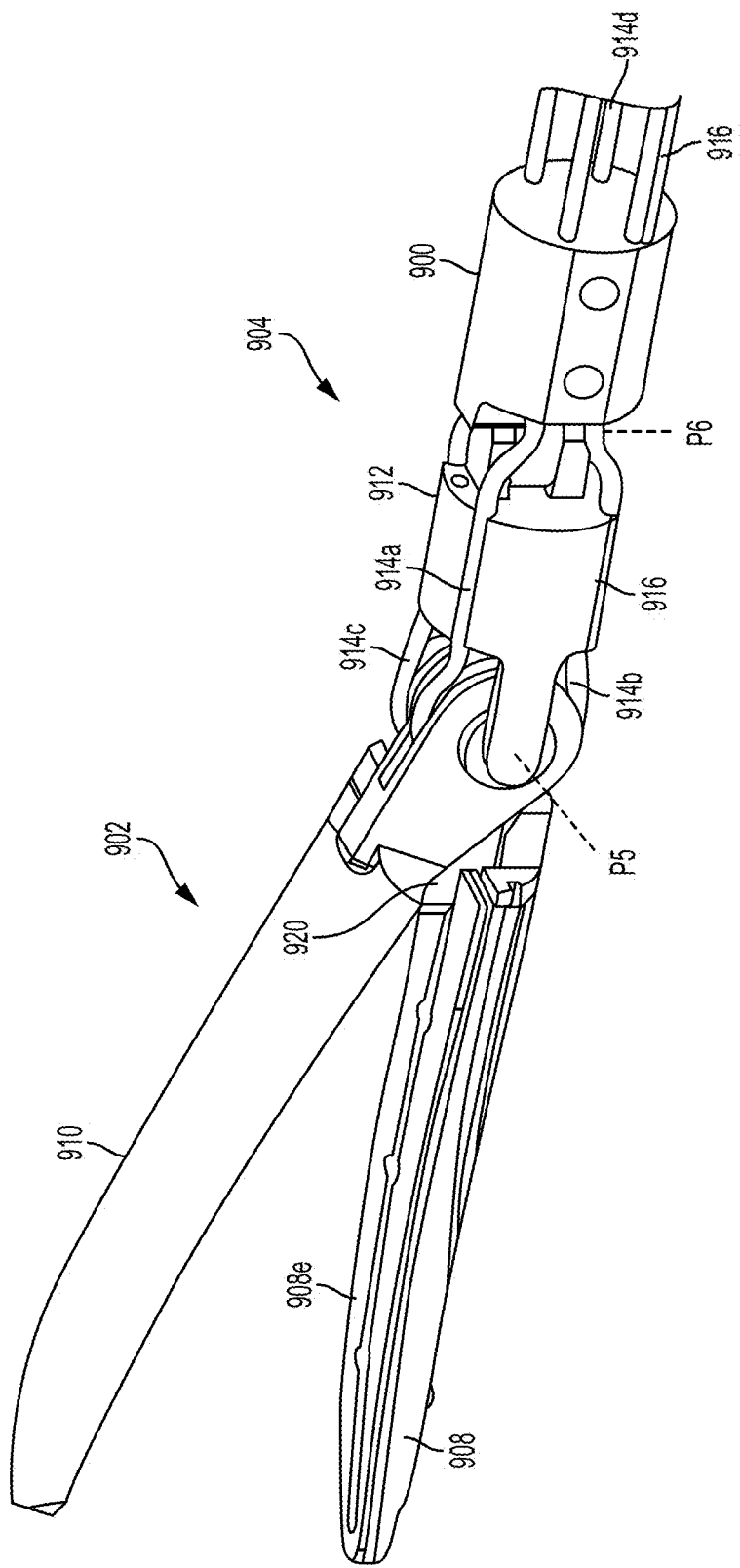
FIG. 46 is a perspective view of a distal portion of yet another embodiment of a surgical tool.
Figure 47:
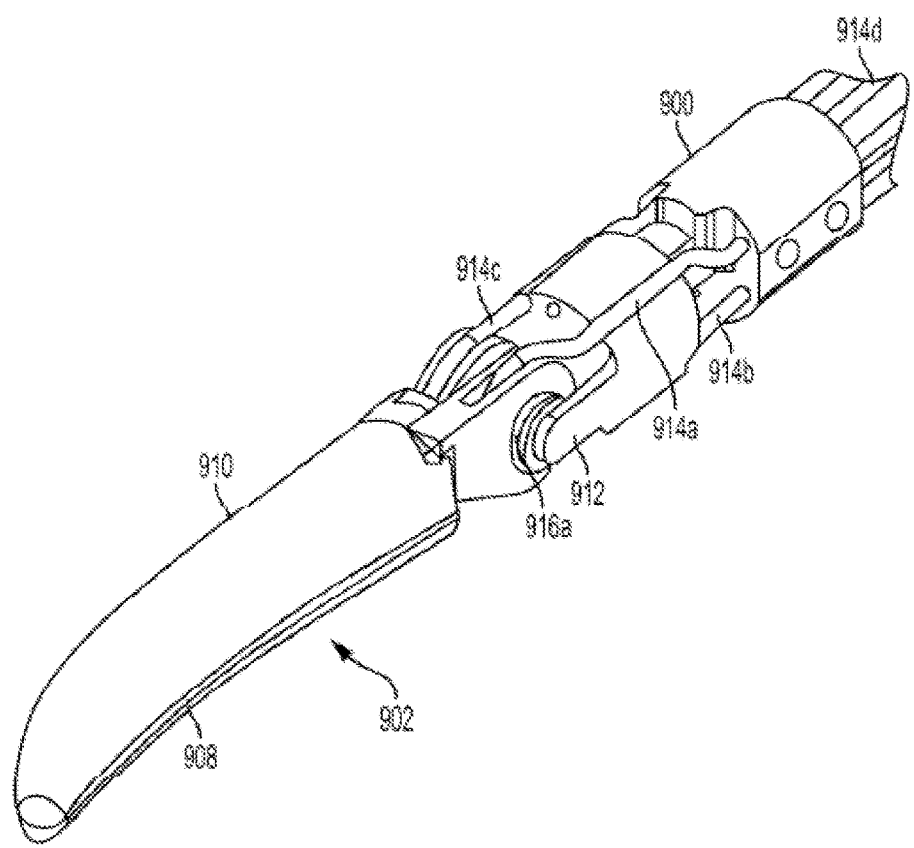
FIG. 47 is a perspective view of a distal portion of the tool of FIG. 46.
Figure 48:
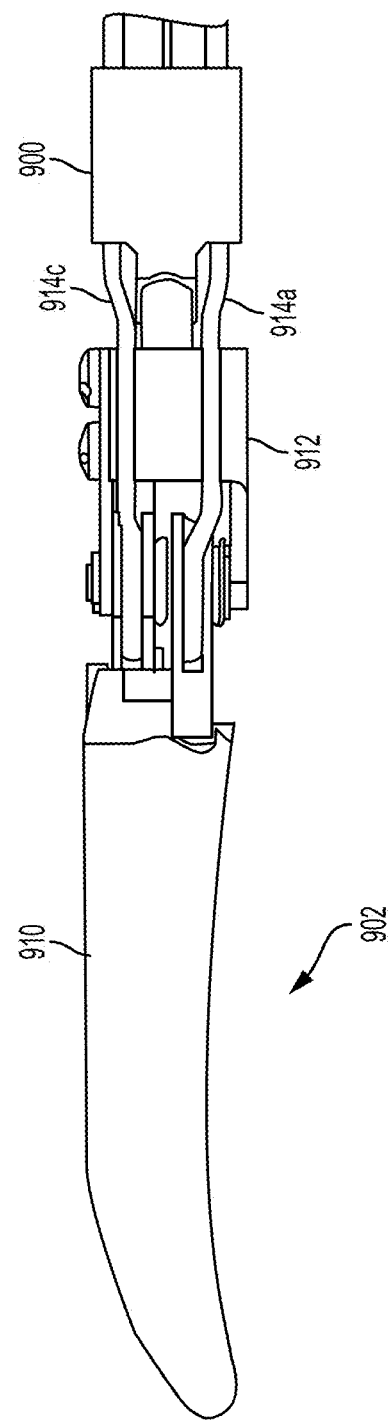
FIG. 48 is a top view of a distal portion of the tool of FIG. 46.

FIG. 45 illustrates another embodiment of a surgical tool 614 configured to apply energy to tissue. The tool 614 is generally configured and used similar to the tool 200 of FIGS. 6-9, e.g., includes an elongate shaft 616, an end effector 618 including upper and lower jaws 620, 622, a wrist 624 that couples the end effector 618 to the shaft 616 at a distal end of the shaft 616, a linkage 634 that couples the end effector 618 and shaft 616 together, a tool housing (not shown) coupled to a proximal end of the shaft 616, a cutting element 620 that translates along the end effector 618, four articulation cables 622, two closure cables, a central tube 624, a pair of links 626 (one of the links is obscured in FIG. 45), an energy cable, a pair of electrical wires 628 for each of the tool's electrodes 630a, 630b, and a cutting element cable 632.

In this illustrated embodiment, the cutting element cable 632 is operatively coupled to a pulley 636 at the end effector 618 to effect translational movement of the cutting element 620 along the end effector 618. One of the trailing ends of the cutting element cable 632 extends proximally from one side of the pulley 636, and the other of the cutting element cable's trailing ends extends proximally from the other side of the pulley 636. Pulling a first one of the cutting element cable's trailing ends proximally, e.g., via input to an input interface at the tool housing, is configured to translate the cutting element 620 distally along the end effector 618, e.g., to cause cutting of tissue engaged by the end effector 618, with the cutting element cable 632 sliding along the pulley 636. When the cutting element 620 is at its distal-most position along the end effector 618, pulling of the first one of the trailing ends of the cutting element cable 632 will not cause movement of the cutting element 620. Pulling the other one of the cutting element cable's trailing ends proximally, e.g., via input to an input interface at the tool housing, is configured to translate the cutting element 620 proximally along the end effector 618, e.g., to retract the cutting element 620, with the cutting element cable 632 sliding along the pulley 636. When the cutting element 620 is at its proximal-most position along the end effector 618, as shown in FIG.

45, pulling of the second one of the trailing ends of the cutting element cable 632 will not cause movement of the cutting element 620. When the end effector 618 is articulated at one or both of the tool's joints 638, 640, the cutting element cable 632 being pulled proximally to actuate the cutting element 620 more easily bends or flexes the cutting element cable 632 at the pivoted one or both of the joints 638, 640, as compared to the cutting element cable 632 being pushed distally. The cutting element cable 632 may thus not be subjected to buckling loads, thereby reducing chances of cable failure and/or increasing an overall life of the cable 632. Including the pulley 636 in the end effector 600, e.g., in the lower jaw 622 as shown, does not add any dead space in the end effector 618.

FIGS. 46-50 illustrate another embodiment of a surgical tool configured to apply energy to tissue. The tool is generally configured and used similar to the tool 10 of FIG. 1, e.g., includes an elongate shaft 900, an end effector 902, a wrist 904 that couples the end effector 902 to the shaft at a distal end of the shaft, and a tool housing 906 coupled to a proximal end of the shaft 900. The end effector 902 in this illustrated embodiment includes opposed lower and upper jaws 908, 910 that each include an electrode 908e, 910e on tissue-facing surfaces thereof. Similar to the tool 200 of FIGS. 6-9, the wrist 904 of the tool includes a linkage 912 configured to facilitate articulation of the end effector 902 relative to the elongate shaft 900 about first and second pivot axes P5, P6.

Figure 49:
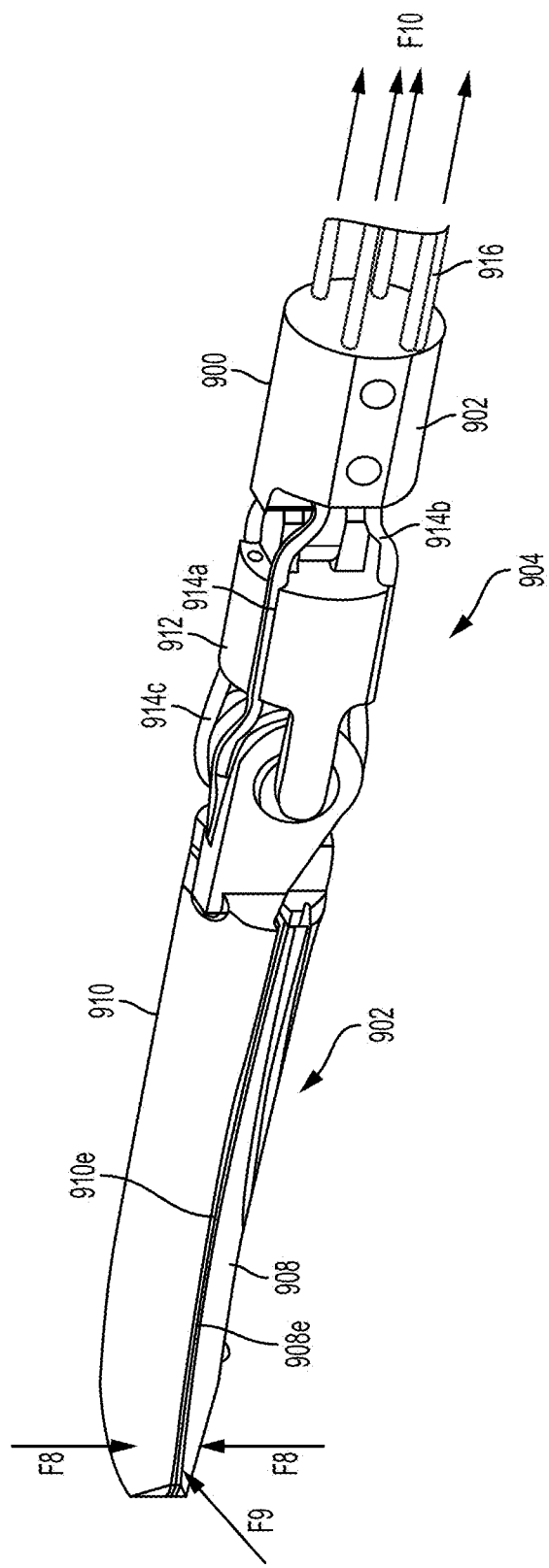
FIG. 49 is another view of a distal portion of the tool of FIG. 46.

The tool includes four articulation and closure cables 914a, 914b, 914c, 914d, with a first pair of articulation and closure cables 914a, 914b on one side of the tool and a second pair of articulation and closure cables 914c, 914d on the opposite side of the tool. Distal ends of the first and second articulation and closure cables 914a, 914b are attached to a first pulley 916a (see FIG. 47) at a distal end of the end effector 902, and distal ends of the third and fourth articulation and closure cables 914c, 914d are attached to a second pulley (obscured in FIG. 47) at the distal end of the end effector 902. The articulation cables 914a, 914b, 914c, 914d are configured to be selectively actuated (e.g., pushed/pulled in response to inputs to input interfaces at the tool housing 906) to cause pivoting motion at one or both of the first and second pivot axes P5, P6 or opening/closing of the jaws 908, 910. The same cables 914a, 914b, 914c, 914d are thus configured to effect both articulation and closing/opening of the end effector 902, which may help simplify manufacturing of the tool and/or allow the tool to be smaller since fewer cables need be used. As shown in FIG. 49, since the same cables 914a, 914b, 914c, 914d can provide articulation and clamping, the clamping force F8 is reduced when a side load F9 is applied and each pair of the cables 914a, 914b, 914c, 914d provide a force F10.

The tool includes an energy cable 916 configured to be actuated to deliver energy to the electrodes 908e, 910e. The tool also includes a cutting element cable 918 (see FIG. 50) configured to effect translational movement of a cutting element 920 along the end effector 902.

In this illustrated embodiment, the tool housing 906 has six input interfaces with first, second, third, and fourth input interfaces for selective articulation and opening/closing of the tool's end effector 902, a fifth input interface for cutting element 920 translation, and a sixth input interface is available for other use. In this illustrated embodiment, the first, second, third, and fourth input interfaces are linear mechanisms, and the fifth and sixth input interfaces are rotary mechanisms.

Figure 50:
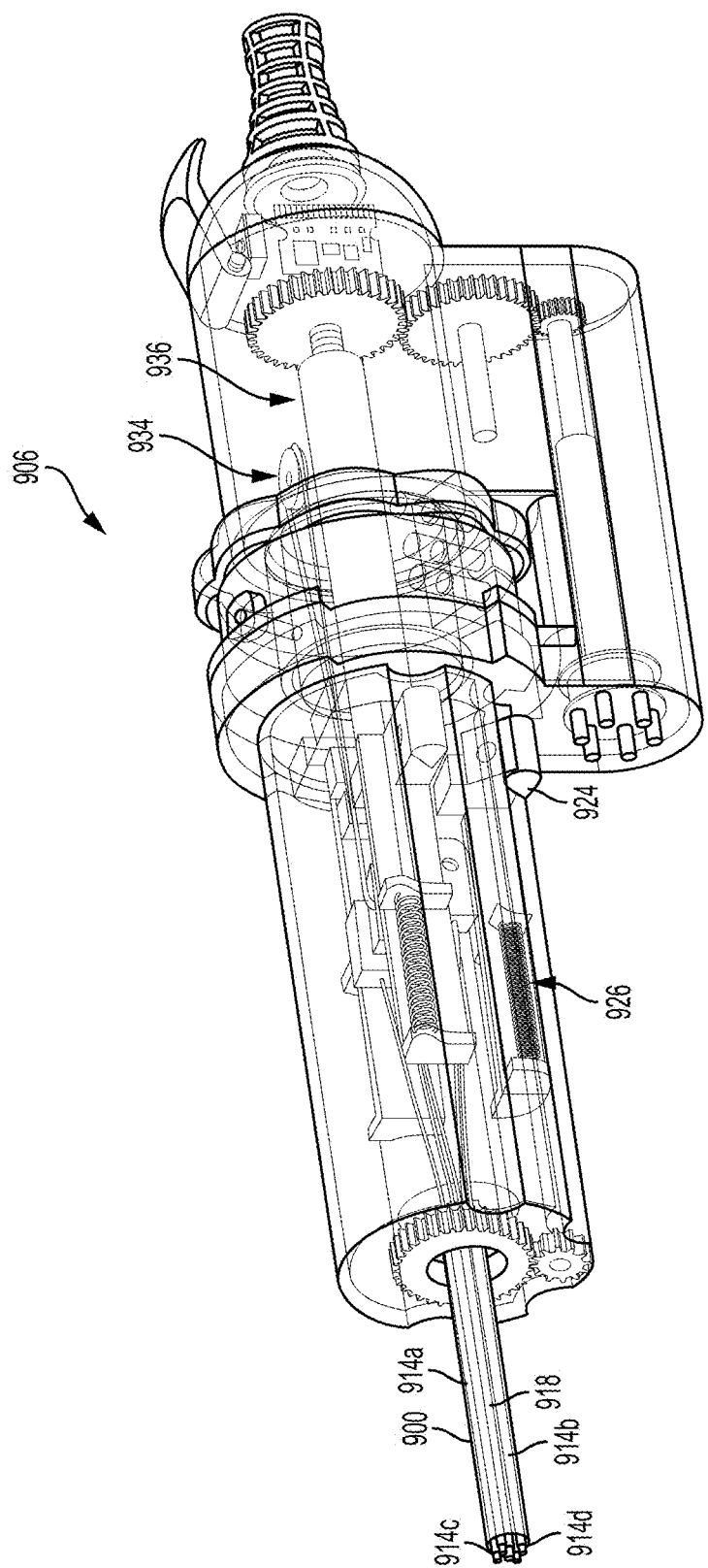
FIG. 50 is a perspective, partially transparent view of a proximal portion of the tool of FIG. 46.
Figure 51:
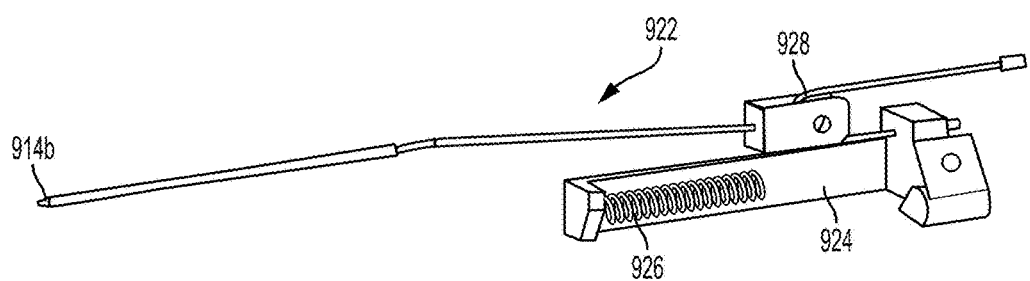
FIG. 51 is a perspective view of an articulation and closure mechanism of the tool of FIG. 50.

As shown in FIG. 50, each of the first, second, third, and fourth input interfaces include an articulation and closure mechanism that includes a translational member configured to longitudinally translate to effect longitudinal translational movement of the one of the cables 914a, 914b, 914c, 914d operatively coupled thereto. FIG. 51 illustrates as a representative example of the four articulation and closure mechanisms one of the articulation and closure mechanisms 922 and translational members 924 for one of the cables 914b. The articulation and closure mechanism 922 also includes a bias element 926, which is in the form of a coil spring in this illustrated embodiment, that biases its associated cable 914b in a distal direction. The articulation and closure mechanism 922 also includes a pulley 928 to direct motion in the appropriate distal direction. The pulley 928 is located in a central position between the actuator mounting points. Each of the articulation and closure mechanisms can be configured, for example, to provide about 10.5 mm of translational articulation and closure cable movement, which can be enough to cause full articulation of the end effector 902 (e.g., +/− about 160°).

Figure 52:
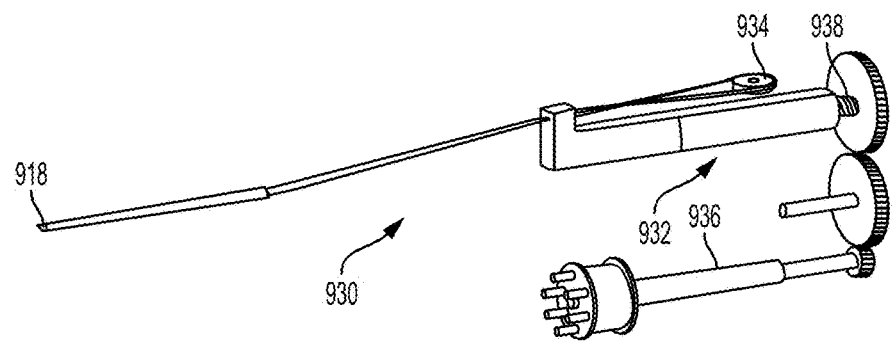
FIG. 52 is a perspective view of a cutting element translation mechanism of the tool of FIG. 50.

As shown in FIGS. 50 and 52, the fifth input interface includes a cutting element translation mechanism 930 that includes a gear system 932 configured to effect longitudinal translational movement of the cutting element cable 918 via an auxiliary motor 936 that is geared to a leadscrew 938. The cutting element translation mechanism 930 also includes a pulley 934 to direct motion in the appropriate distal direction. Sensitivity of the cutting element translation mechanism 930 can be adjusted by changing the gearing and lead screw pitch. The cutting element translation mechanism 930 can be configured, for example, to provide about 24 mm of cutting element translational movement to fully translate the cutting element fully along the end effector 902.

Figure 53:
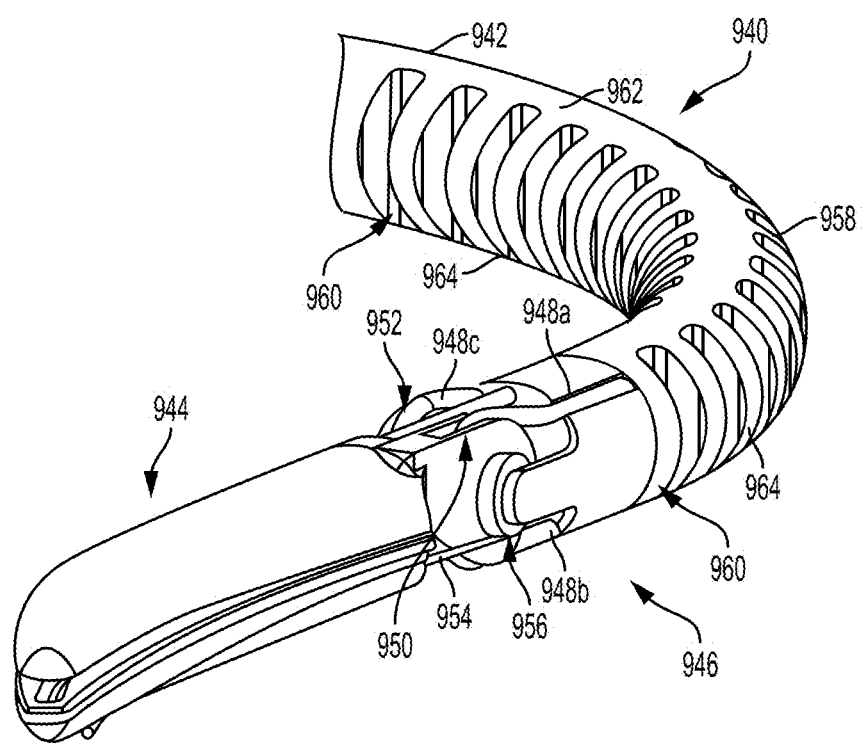
FIG. 53 is a perspective view of a distal portion of still another embodiment of a surgical tool.
Figure 54:
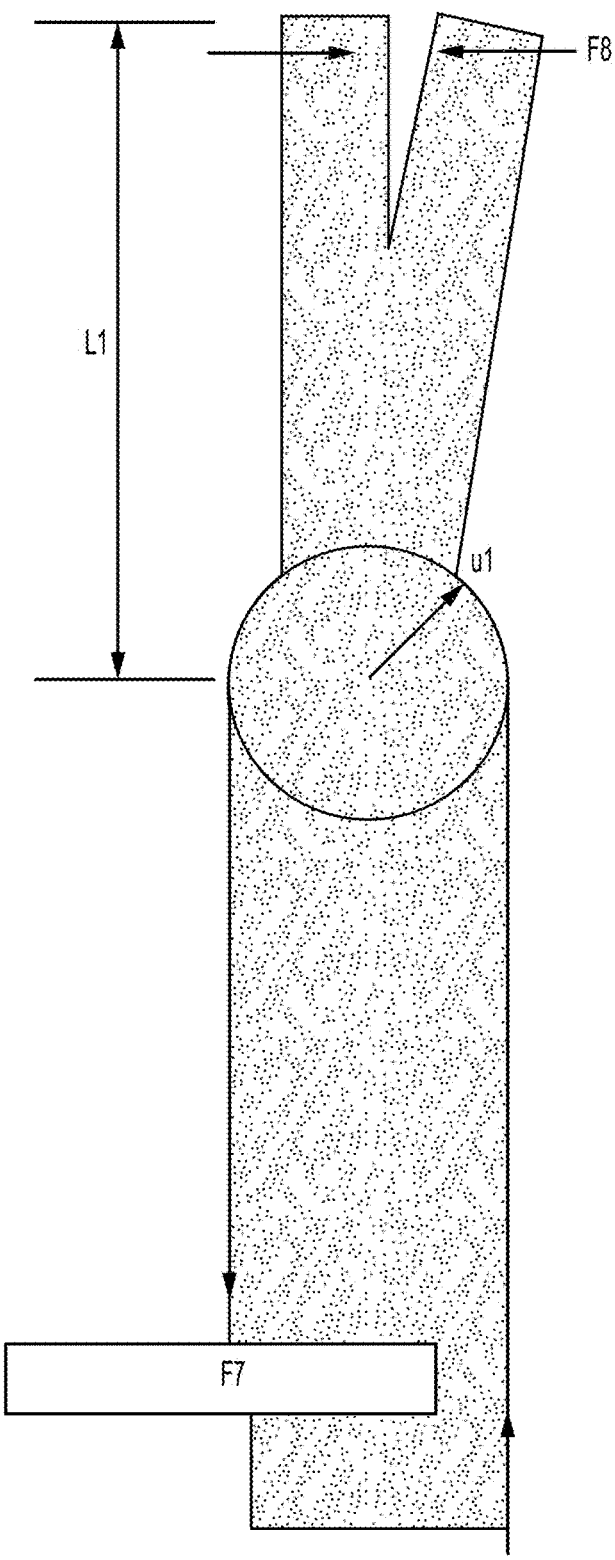
FIG. 54 is a schematic view of forces on the tool of FIG. 53.

FIG. 53 illustrates another embodiment of a surgical tool 940 configured to apply energy to tissue. The tool 940 is generally configured and used similar to the tool of FIGS. 46-50, e.g., includes an elongate shaft 942, an end effector 944, a wrist 946 that couples the end effector 944 to the shaft 942 at a distal end of the shaft 942, a tool housing (not shown) coupled to a proximal end of the shaft 942, four articulation and closure cables 948a, 948b, 948c (the fourth cable is obscured in FIG. 53), a first pulley 950 operatively engaged with the first and second cables 948a, 948b, a second pulley 952 operatively engaged with the third and fourth cables 948c, an energy cable 954, a third pulley 956 operatively engaged with the energy cable 954, and a cutting element cable (obscured in FIG. 53). In this illustrated embodiment, the wrist 946 does not any pivoting linkages but instead includes a flexible neck 958. The flexible neck 958 is configured to bend laterally (e.g., in left and right directions) to facilitate articulation of the end effector 944 laterally. The flexible neck 958 is made from one or more flexible materials, e.g., a polyetherimide (PEI) material (such as ULTEM™ resin), polyetheretherketone (PEEK), polycarbonate, nylon, high density polyethylene, polyester, polytetrafluoroethylene, polypropylene, polyvinylchlorideto, etc. The flexible neck 958 includes two rows of slots 960 formed in opposite sides thereof that define first and second opposed longitudinal spines 962 (one of the spines is obscured in FIG. 53) and first and second rows of arcuate ribs 964 extending between the spines along a circumference of the flexible neck 958. Exemplary embodiments of flexible necks are further described in U.S. Pat. No. 9,402,682 entitled "Articulation Joint Features For Articulating Surgical Device" filed on Sep. 19, 2011, and in U.S. Pat. Pub. No. 2016/0270839 entitled "Flexible Neck For Surgical Instruments" filed on Mar. 16, 2015, which are hereby incorporated by reference in their entireties.

Depending on a length of the flexible neck 958, full articulation F7 of the end effector 944 can take various articulation cable forces, in this example in which the end effector 944 has a length L1 of about 28.6 mm and an opening radius U1 of about 2.375 mm. Available articulation force F7 in an articulation and closure cable can "use up" about 20% of the available force F7. To fully articulate the end effector 944 in the direction of end effector closure or clamping, the articulation and closure cable can travel about 8 mm. Doubling the cable force at the tool's proximal end leave about 12.5 mm of cable travel available at the tool's distal end, which is enough travel to achieve full end effector articulation. Without any extra forces considered (friction, articulation force), the articulation force F7 results in a clamping force F8. If force need to articulate the flexible neck 958 is included, at full articulation the end effector clamping force is reduced.

Figure 55:
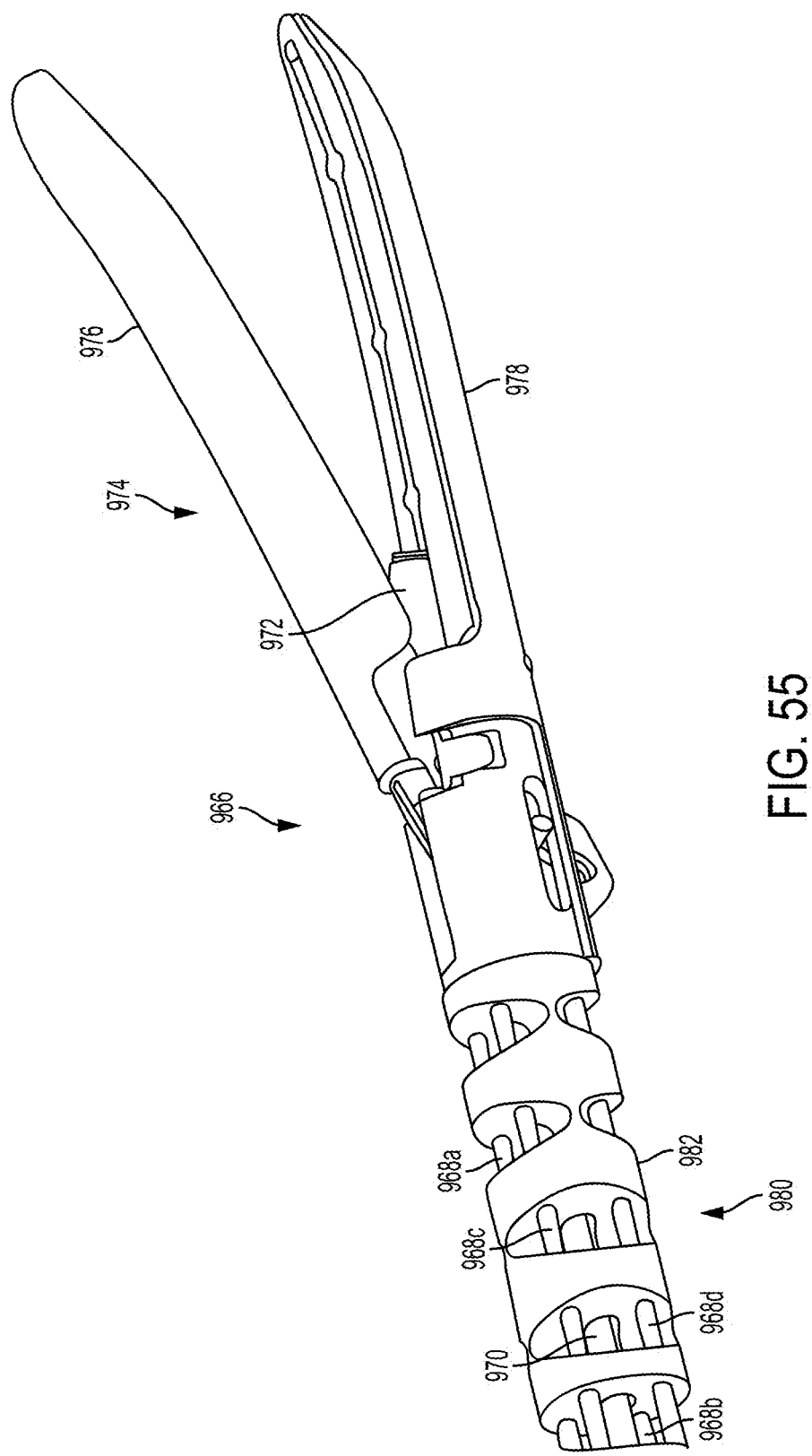
FIG. 55 is a perspective view of a distal portion of another embodiment of a surgical tool.
Figure 56:
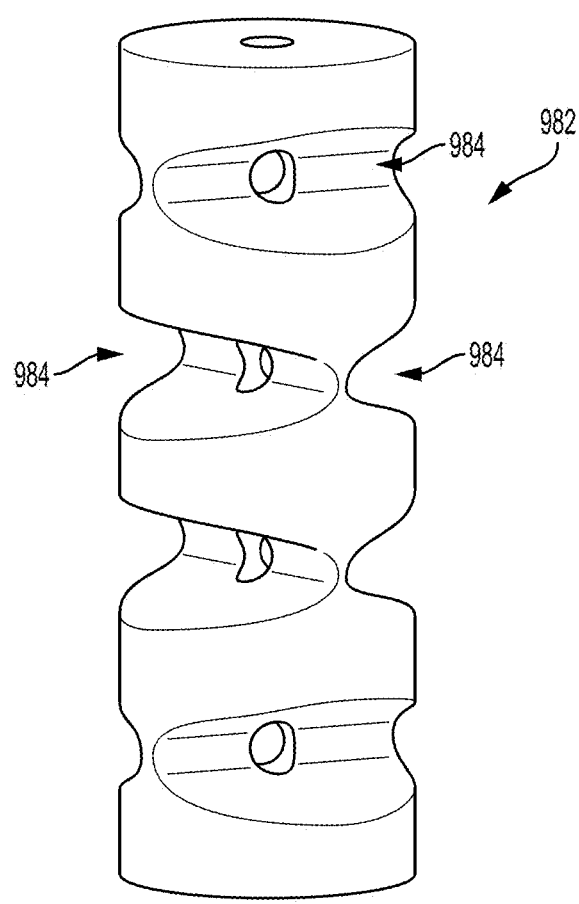
FIG. 56 is a perspective view of a flexible neck of the tool of FIG. 55.
Figure 57:
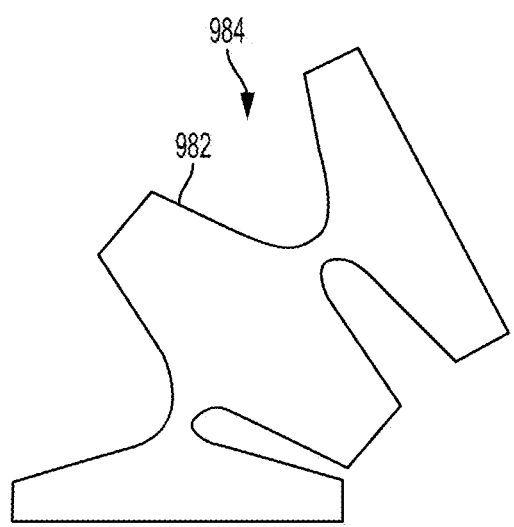
FIG. 57 is a side, partial view of the flexible neck of FIG. 55 with the flexible neck flexed.
Figure 58:
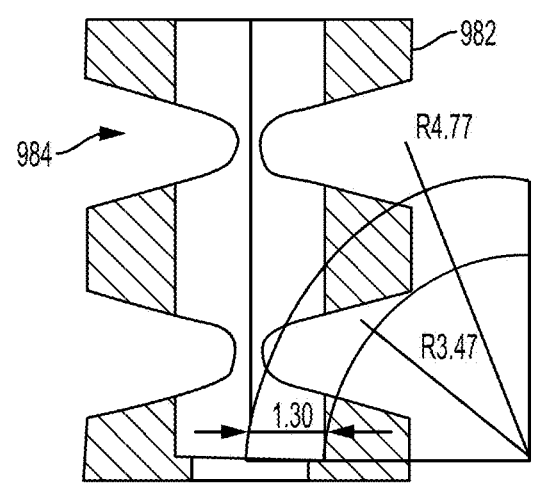
FIG. 58 is a side, partial view of the flexible neck of FIG. 55 with the flexible neck unflexed.

FIG. 55 illustrates another embodiment of a surgical tool 966 configured to apply energy to tissue. The tool 966 is generally configured and used similar to the tool of FIG. 53, e.g., includes an elongate shaft (not shown), an end effector 974, a wrist 980 that couples the end effector 974 to the shaft at a distal end of the shaft, a tool housing (not shown) coupled to a proximal end of the shaft, four articulation and closure cables 968a, 968b, 968c, 968d, a first pulley (obscured in FIG. 55) operatively engaged with the first and second cables 968a, 968b, a second pulley (obscured in FIG. 55) operatively engaged with the third and fourth cables 968c, 968d, an energy cable (obscured in FIG. 55), and a cutting element cable 970 for translation of a cutting element 972 along upper and lower jaws 976, 978 of the end effector 974. In this illustrated embodiment, the wrist 980 includes a flexible neck 982, also shown in FIG. 56, that is generally configured and used similar to the flexible neck 958 of the tool of FIG. 53. As shown in FIGS. 57 and 58, the flexible neck 982 has two flexion joints 984 per plane. Each of the joints 984 in this illustrated embodiment is configured to undergo about 40° of flexion for a total of about 80° flexion for pitch and yaw motion.

Figure 59:
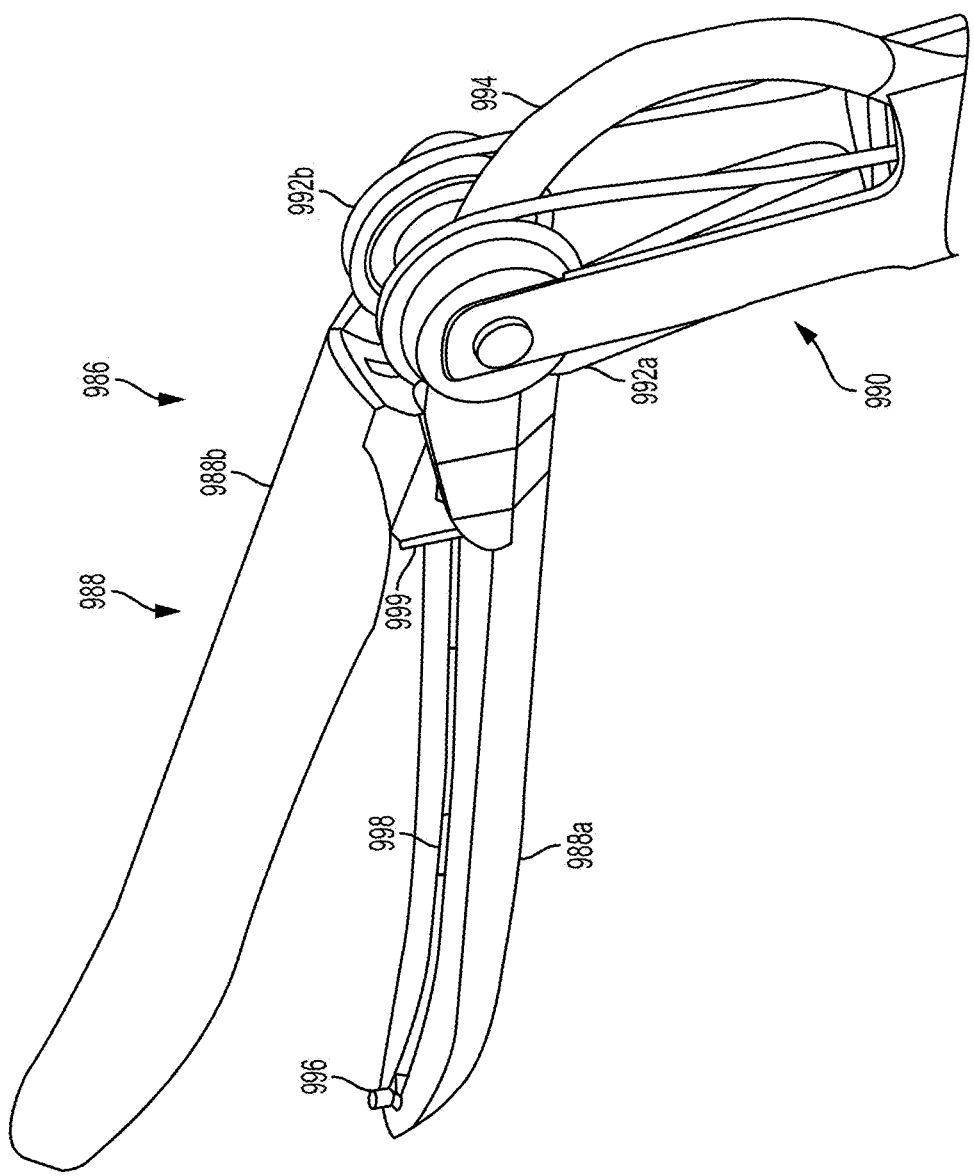
FIG. 59 is a perspective view of a distal portion of still another embodiment of a surgical tool.

FIG. 59 illustrates another embodiment of a surgical tool 986 configured to apply energy to tissue. The tool 986 is generally configured and used similar to the tool of FIGS. 46-50, e.g., includes an elongate shaft (not shown), an end effector 988, a wrist 990 that couples the end effector 988 to the shaft at a distal end of the shaft, a tool housing (not shown) coupled to a proximal end of the shaft, two articulation and closure cables 992a, 992b, and a cutting element cable 994. The end effector 988 includes a single spacer 996 at a distal end of a longitudinal slot 998 through which a cutting element 999 translates along the end effector 988, similar to the spacer 610 of FIGS. 43-44A. In this illustrated embodiment, one of the articulation and closure cables 992a is operatively engaged with a lower jaw 988a of the end effector 988 by being looped around a distal end thereof, and the other of the articulation and closure cables 992b is operatively engaged with an upper jaw 988b of the end effector 988 by being looped around a distal end thereof. Selective movement of one or both of the cables 992a, 992b is configured to selectively articulate the end effector 988 and open/close the jaws 988a, 988b.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 60:
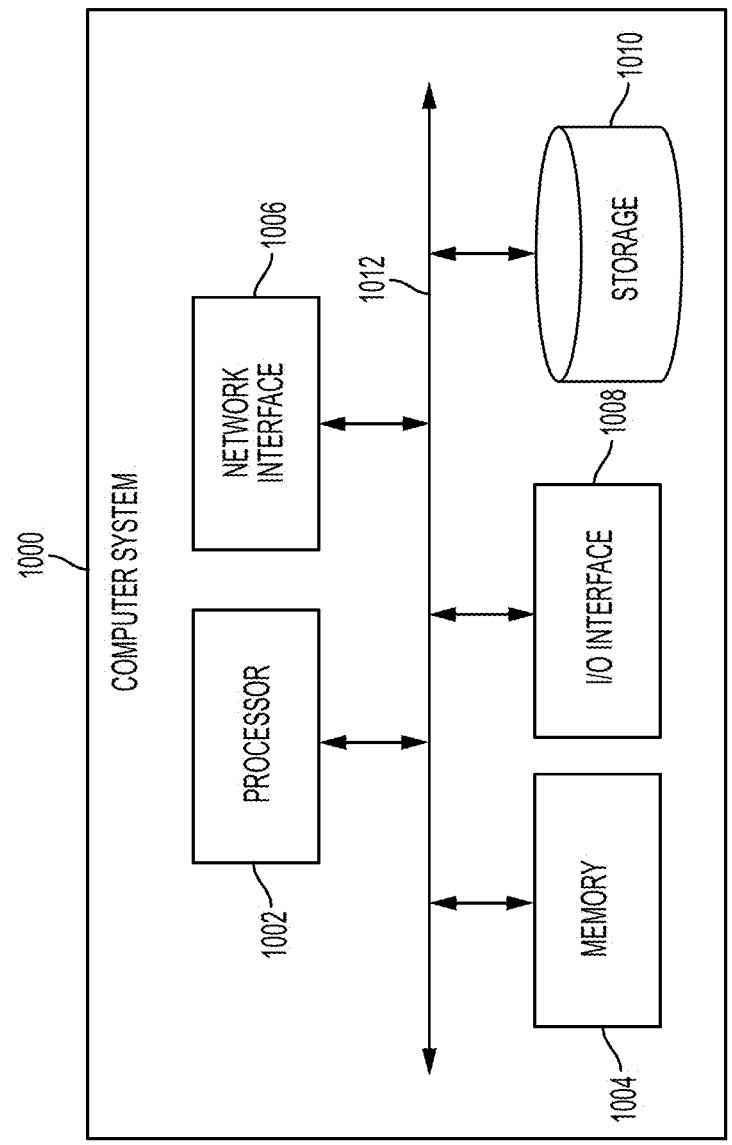
FIG. 60 is a schematic view of one embodiment of a computer system.

FIG. 60 illustrates one exemplary embodiment of a computer system 1000. As shown, the computer system 1000 includes one or more processors 1002 which can control the operation of the computer system 1000. "Processors" are also referred to herein as "controllers." The processor(s) 1002 can include any type of microprocessor or central processing unit (CPU), including programmable general-purpose or special-purpose microprocessors and/or any one of a variety of proprietary or commercially available single or multi-processor systems. The computer system 1000 can also include one or more memories 1004, which can provide temporary storage for code to be executed by the processor(s) 1002 or for data acquired from one or more users, storage devices, and/or databases. The memory 1004 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 1000 can be coupled to a bus system 1012. The illustrated bus system 1012 is an abstraction that represents any one or more separate physical busses, communication lines/interfaces, and/or multi-drop or point-to-point connections, connected by appropriate bridges, adapters, and/or controllers. The computer system 1000 can also include one or more network interface(s) 1006, one or more input/output (IO) interface(s) 1008, and one or more storage device(s) 1010.

The network interface(s) 1006 can enable the computer system 1000 to communicate with remote devices, e.g., other computer systems, over a network, and can be, for non-limiting example, remote desktop connection interfaces, Ethernet adapters, and/or other local area network (LAN) adapters. The IO interface(s) 1008 can include one or more interface components to connect the computer system 1000 with other electronic equipment. For non-limiting example, the IO interface(s) 1008 can include high speed data ports, such as universal serial bus (USB) ports, 1394 ports, Wi-Fi, Bluetooth, etc. Additionally, the computer system 1000 can be accessible to a human user, and thus the IO interface(s) 1008 can include displays, speakers, keyboards, pointing devices, and/or various other video, audio, or alphanumeric interfaces. The storage device(s) 1010 can include any conventional medium for storing data in a non-volatile and/or non-transient manner. The storage device(s) 1010 can thus hold data and/or instructions in a persistent state, i.e., the value(s) are retained despite interruption of power to the computer system 1000. The storage device(s) 1010 can include one or more hard disk drives, flash drives, USB drives, optical drives, various media cards, diskettes, compact discs, and/or any combination thereof and can be directly connected to the computer system 1000 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 60 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 1000 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 1000 can also include a web server for generating and/or delivering the web pages to client computer systems.

In an exemplary embodiment, the computer system 1000 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
    an elongate shaft;
    a pair of jaws at a distal end of the elongate shaft, the pair of jaws being configured to engage tissue therebetween and apply energy thereto;
    a cable configured to be actuated and thereby move in a proximal direction;

a slidable member operatively engaged with the cable and being configured to slide in a distal direction in response to the movement of the cable in the proximal direction; and a link operatively coupled with the slidable member and with the cable, the sliding of the slidable member being configured to cause the link to pivot and thereby cause the pair of jaws to open.

2. The device of claim 1, further comprising a second cable operatively engaged with the slidable member and configured to move in the proximal direction to cause the pair of jaws to close, the slidable member being configured to slide in the proximal direction in response to the movement of the second cable in the proximal direction, and the sliding of the slidable member in the proximal direction being configured to cause the link to pivot and thereby cause the pair of jaws to close.

3. The device of claim 2, wherein the cable is attached to one of a proximal end and a distal end of the slidable member, and the second cable is attached to the other of the proximal end and the distal end of the slidable member.

4. The device of claim 2, wherein the cable is configured to move in the distal direction when the second cable is moving in the proximal direction, and the second cable is configured to move in the distal direction when the cable is moving in the proximal direction.

5. The device of claim 2, further comprising a housing having the elongate shaft extending distally therefrom, the housing including a first rotary member configured to rotate to cause the movement of the cable in the distal direction and including a second rotary member configured to rotate to cause the movement of the second cable in the proximal direction.

6. The device of claim 5, wherein the housing is configured to be coupled to a tool driver of a robotic surgical system that provides inputs to the first and second rotary members to cause the rotation thereof.

7. The device of claim 1, further comprising a pulley having the cable operatively engaged therewith, with trailing ends of the cable extending proximally from the pulley.

8. The device of claim 1, wherein the cable is configured to be actuated and thereby move in the distal direction, the slidable member being configured to slide in the proximal direction in response to the movement of the cable in the distal direction, and the sliding of the slidable member in the proximal direction being configured to cause the link to pivot and thereby cause the pair of jaws to close.

9. The device of claim 1, further comprising a housing having the elongate shaft extending distally therefrom, the housing including a first rotary member configured to rotate to cause the movement of the cable in the proximal direction.

10. The device of claim 1, further comprising a rod extending along the elongate shaft, the slidable member being configured to slide along the rod.

11. The device of claim 1, further comprising a bias member that biases the pair of jaws closed.

12. The device of claim 1, further comprising an articulation cable configured to be actuated and thereby cause the pair of jaws to articulate relative to the elongate shaft; and an energy cable configured to deliver energy for the pair of jaws to apply to the engaged tissue.

13. A surgical device, comprising:
an elongate shaft;
an end effector configured to engage tissue and apply energy thereto;
a cutting element configured to move longitudinally along the end effector to cut tissue engaged by the end effector;
a cutting element cable configured to be actuated to cause the movement of the cutting element; and
a pulley at a distal end of the end effector and operatively coupled to the cutting element cable such that the cutting element cable slides along the pulley during the movement of the cutting element.

14. The device of claim 13, wherein the cutting element cable is configured to be pushed distally to cause the movement of the cutting element.

15. The device of claim 13, further comprising an articulation cable configured to be actuated and thereby cause the pair of jaws to articulate relative to the elongate shaft;
a closure cable configured to be actuated and thereby cause the pair of jaws to close; and
an energy cable to configured to deliver energy for the pair of jaws to apply to the engaged tissue.

16. A surgical method, comprising:
advancing jaws at a distal end of a surgical tool into a patient, the surgical tool being configured to apply energy to tissue engaged by the end effector; and
causing a cable that extends along the elongate shaft to move proximally to thereby cause a slidable member operatively engaged with the cable to slide distally, the distal sliding of the slidable member causing a link to pivot and thereby cause the jaws to open.

17. The method of claim 16, further comprising causing a second cable that extends along the elongate shaft to move proximally to thereby cause the slidable member operatively engaged with the second cable to slide proximally, the proximal sliding of the slidable member in response to the movement of the second cable causing the link to pivot and thereby cause the jaws to close.

18. The method of claim 17, wherein causing the cable to move proximally includes providing an input to the surgical tool from a robotic surgical system having the surgical tool coupled thereto, and causing the second cable to move proximally includes providing another input to the surgical tool from the robotic surgical system having the surgical tool coupled thereto.

19. The method of claim 16, further comprising causing the cable to move distally to thereby cause the slidable member to slide proximally, the proximal sliding of the slidable member causing the link to pivot and thereby cause the jaws to close.

20. The method of claim 16, wherein causing the cable to move proximally includes providing an input to the surgical tool from a robotic surgical system having the surgical tool coupled thereto.

* * * * *